(12) United States Patent
Nitert et al.

(10) Patent No.: US 11,795,180 B2
(45) Date of Patent: Oct. 24, 2023

(54) FORMULATION OF A PAN-JAK INHIBITOR

(71) Applicant: THERAVANCE BIOPHARMA R&D IP, LLC, South San Francisco, CA (US)

(72) Inventors: Bernardus Joseph Nitert, Dieden (NL); Yvonne Rosiaux, Rijkevorsel (BE); Marian E. Van Der Veen, Eindhoven (NL); Nathan Schulpen, Antwerp (BE); Jens Maes, Herentals (BE); Guido Verniest, Knesselare (BE); Venkat R. Thalladi, Foster City, CA (US); Ai Ling Ching, San Francisco, CA (US)

(73) Assignee: THERAVANCE BIOPHARMA R&D IP, LLC, South San Francisco, CA (US)

( * ) Notice: Subject to any disclaimer, the term of this patent is extended or adjusted under 35 U.S.C. 154(b) by 16 days.

(21) Appl. No.: 17/450,205

(22) Filed: Oct. 7, 2021

(65) Prior Publication Data

US 2022/0112220 A1   Apr. 14, 2022

Related U.S. Application Data

(60) Provisional application No. 63/089,928, filed on Oct. 9, 2020.

(51) Int. Cl.
| | | |
|---|---|---|
| *A61K 31/46* | (2006.01) | |
| *C07D 519/00* | (2006.01) | |
| *A61K 47/02* | (2006.01) | |
| *A61K 47/38* | (2006.01) | |

(52) U.S. Cl.
CPC ............ *C07D 519/00* (2013.01); *A61K 47/02* (2013.01); *A61K 47/38* (2013.01)

(58) Field of Classification Search
CPC ...................................................... A61K 31/46
See application file for complete search history.

(56) References Cited

U.S. PATENT DOCUMENTS 9,725,470 B2 * 8/2017 Hudson .................. A61P 29/00

OTHER PUBLICATIONS

International Search Report and Written Opinion for International Application No. PCT/US2021/054004 dated Jan. 20, 2022, 13 pages.

* cited by examiner

*Primary Examiner* — John S Kenyon
(74) *Attorney, Agent, or Firm* — Brian C. Trinque; Lathrop GPM LLP

(57) ABSTRACT

The present disclosure relates to pharmaceutical compositions comprising (3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile), methods of use thereof, and methods of preparation.

24 Claims, 9 Drawing Sheets

FORMULATION OF A PAN-JAK INHIBITOR

CROSS-REFERENCE TO RELATED APPLICATIONS

This application claims the benefit under 35 U.S.C. § 119(e) of U.S. Provisional Patent Application No. 63/089,928, filed Oct. 9, 2020, the entire disclosure of which is hereby incorporated herein by reference.

BACKGROUND

The inflammatory bowel diseases (IBDs), such as ulcerative colitis (UC) and Crohn's disease (CD), adversely impact the quality of life of patients. The disorders are associated with rectal bleeding, diarrhea, abdominal pain, weight loss, nausea and vomiting, and also lead to an increased incidence of gastrointestinal cancers. The direct and indirect societal costs of IBD are substantial.

Because inhibition of the Janus kinase ("JAK") family of enzymes could inhibit signaling of many key pro-inflammatory cytokines, JAK inhibitors may be useful in the treatment of UC and other inflammatory diseases such as CD, allergic rhinitis, asthma, and chronic obstructive pulmonary disease (COPD). However, due to the modulating effect of the JAK/STAT pathway on the immune system, systemic exposure to JAK inhibitors may have an adverse systemic immunosuppressive effect. Therefore, it would be desirable to provide new JAK inhibitors that are locally acting at the site of action without significant systemic effects. In particular, for the treatment of gastrointestinal inflammatory diseases, such as UC and CD, it would be desirable to provide new pharmaceutical compositions comprising JAK inhibitors which can be administered orally and achieve therapeutically relevant exposure in the gastrointestinal tract with minimal systemic exposure.

As discussed in U.S. Pat. Nos. 9,725,470 and 10,072,026, (3-((1R,3s,5S)-3-((7-((5-methyl-1H-pyrazol-3-yl)amino)-1,6-naphthyridin-5-yl)amino)-8-azabicyclo[3.2.1]octan-8-yl) propanenitrile) is a potent pan-JAK inhibitor that may have clinical potential in an inflammatory bowel disease such as UC and CD. This compound is referred to herein as Compound I.

As discussed above, the ongoing need to treat UC and other inflammatory diseases such as Crohn's Disease, coupled with the potent pan-JAK inhibitor activity of Compound I, demonstrates that there is a need for chemically stable formulations of Compound I that are suitable for use on a commercial scale. The formulations of Compound I disclosed herein meet this and other needs.

SUMMARY

The present disclosure provides, inter alia, a pharmaceutical composition comprising Compound I:

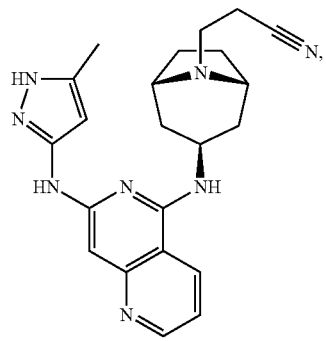 [SMILES: Cc1cc(Nc2cc3ncccc3c(N[C@@H]3C[C@H]4CC[C@@H](C3)N4CCC#N)n2)n[nH]1]

or a pharmaceutically acceptable salt thereof; microcrystalline cellulose; lactose; silicon dioxide; magnesium stearate; a disintegrant; and optionally a coating.

In some embodiments, the present disclosure provides, inter alia, a pharmaceutical composition comprising Compound I:

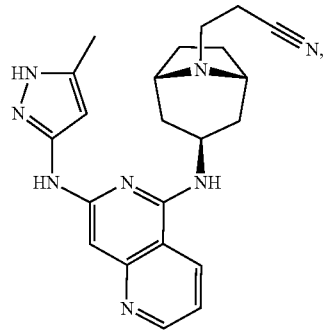 [SMILES: Cc1cc(Nc2cc3ncccc3c(N[C@@H]3C[C@H]4CC[C@@H](C3)N4CCC#N)n2)n[nH]1]

or a pharmaceutically acceptable salt thereof; microcrystalline cellulose; lactose monohydrate; silicon dioxide; magnesium stearate; a disintegrant; and optionally a coating.

In some embodiments, the disintegrant is low-substituted hydroxypropyl cellulose (L-HPC).

In some embodiments, the pharmaceutical composition comprises about 10 wt % to about 30 wt % of Compound I, or a pharmaceutically acceptable salt thereof; about 31.5 wt % to about 51.5 wt % microcrystalline cellulose; about 20.5 wt % to about 40.5 wt % lactose; about 0.5 wt % to about 1.5 wt % hydrophobic colloidal silicon dioxide; about 0.5 wt % to about 6.5 wt % magnesium stearate; about 0.5 wt % to about 7.5 wt % L-HPC; and optionally a coating.

In some embodiments, the pharmaceutical composition comprises about 20 wt % of Compound I, or a pharmaceutically acceptable salt thereof; about 41.5 wt % microcrystalline cellulose; about 30.5 wt % lactose; about 1.0 wt % hydrophobic colloidal silicon dioxide; about 3.0 wt % magnesium stearate; about 4.0 wt % L-HPC; and optionally a coating.

In some embodiments, the pharmaceutical composition comprises 20 wt % of Compound I, or a pharmaceutically acceptable salt thereof; 41.5 wt % microcrystalline cellulose; 30.5 wt % lactose; 1.0 wt % hydrophobic colloidal silicon dioxide; 3.0 wt % magnesium stearate; 4.0 wt % L-HPC; and optionally a coating.

In some embodiments, the pharmaceutical composition comprises about 10 wt % to about 30 wt % of Compound I, or a pharmaceutically acceptable salt thereof; about 31.5 wt % to about 51.5 wt % microcrystalline cellulose; about 20.5 wt % to about 40.5 wt % lactose monohydrate; about 0.5 wt % to about 1.5 wt % hydrophobic colloidal silicon dioxide; about 0.5 wt % to about 6.5 wt % magnesium stearate; about 0.5 wt % to about 7.5 wt % L-HPC; and optionally a coating.

In some embodiments, the pharmaceutical composition comprises about 20 wt % of Compound I, or a pharmaceutically acceptable salt thereof; about 41.5 wt % microcrystalline cellulose; about 30.5 wt % lactose monohydrate; about 1.0 wt % hydrophobic colloidal silicon dioxide; about 3.0 wt % magnesium stearate; about 4.0 wt % L-HPC; and optionally a coating.

In some embodiments, the pharmaceutical composition comprises 20 wt % of Compound I, or a pharmaceutically acceptable salt thereof; 41.5 wt % microcrystalline cellulose; 30.5 wt % lactose monohydrate; 1.0 wt % hydrophobic colloidal silicon dioxide; 3.0 wt % magnesium stearate; 4.0 wt % L-HPC; and optionally a coating.

In some embodiments, Compound I exhibits a purity of at least 97% purity as measured by UHPLC assay. In some embodiments, Compound I exhibits a purity of at least 99% purity as measured by HPLC assay.

In some embodiments, Compound I is present in a crystalline form characterized by a XRPD diffractogram having peaks expressed in degrees-2-theta at angles (±0.20) of 7.82, 12.82, 15.76, and 20.51. In some embodiments, Compound I is present in a crystalline form characterized by a XRPD diffractogram having peaks expressed in degrees-2-theta at angles (±0.20) of 7.82, 10.75, 12.82, 13.41, 13.59, 14.62, 15.08, 15.50, 15.76, 17.68, 20.51, 20.99, 22.18, 22.87, and 23.73. In some embodiments, Compound I is present in a crystalline form characterized by a XRPD diffractogram having peaks expressed in degrees-2-theta at angles (±0.20) of 7.88, 12.85, 15.80, and 20.41. In some embodiments, Compound I is present in a crystalline form characterized by a XRPD diffractogram having peaks expressed in degrees-2-theta at angles (±0.20) of 7.88, 10.80, 12.85, 13.46, 13.65, 14.65, 15.10, 15.55, 15.80, 17.72, 20.41, 21.00, 22.26, 22.93, and 23.65. In some embodiments, Compound I is present in a crystalline form characterized by a XRPD diffractogram having peaks expressed in degrees-2-theta at angles (±0.20) of 7.87, 12.78, 15.78, and 20.41. In some embodiments, Compound I is present in a crystalline form characterized by a XRPD diffractogram having peaks expressed in degrees-2-theta at angles (±0.20) of 7.87, 10.80, 12.78, 13.47, 13.64, 14.66, 15.11, 15.54, 15.78, 17.75, 20.41, 21.00, 22.22, 22.93, and 23.65.

In some embodiments, Compound I is present in a crystalline form characterized by substantially uniform particle size. In some embodiments, the Dv50 particle size is about 20 μm to about 26 μm as measured by static image analysis. In some embodiments, the Dv50 particle size is about 13 μm to about 15 μm as measured by dry dispersion laser diffraction.

In some embodiments, the microcrystalline cellulose is partially depolymerized alphacellulose. In some embodiments, the lactose is a spray-dried mixture of crystalline lactose monohydrate and amorphous lactose.

In some embodiments, the silicon dioxide is hydrophobic colloidal silicon dioxide. In some embodiments, the silicon dioxide is fumed silica (silicon dioxide) after-treated with dimethyldichlorosilane. In some embodiments, the hydrophobic colloidal silicon dioxide is Aerosil® R972.

In some embodiments, the magnesium stearate has a specific surface area of between 6 and 10 m²/g and a median particle size of between 7 and 11 μm. In some embodiments, the L-HPC has about 7.0% to about 16.0% hydroxypropoxy content. In some embodiments, the L-HPC has about 7.0% to about 9.9% hydroxypropoxy content. In some embodiments, the L-HPC has about 10.0% to about 12.9% hydroxypropoxy content. In some embodiments, the L-HPC has about 13.0% to about 15.9% hydroxypropoxy content. In some embodiments, the L-HPC has about 5.0% to about 16.0% hydroxypropoxy content and a Dv50 particle size from about 35 μm to about 55 μm. In some embodiments, the L-HPC has about 7.0% to about 15.9% hydroxypropoxy content and a Dv50 particle size from about 35 μm to about 55 μm. In some embodiments, the L-HPC has about 10.0% to about 12.9% hydroxypropoxy content and a Dv50 particle size from about 35 μm to about 55 μm.

In some embodiments, the pharmaceutical composition further comprises a coating. In some embodiments, the coating is a polyvinyl alcohol-based film coating. In some embodiments, the polyvinyl alcohol-based film coating comprises poly(vinyl alcohol), glycerol monocaprylocaprate type I, titanium dioxide, and talc. In some embodiments, the polyvinyl alcohol-based film coating comprises poly(vinyl alcohol), glycerol monocaprylocaprate type I, titanium dioxide, talc, and sodium lauryl sulfate. In some embodiments, the polyvinyl alcohol-based film coating further comprises iron oxides. In some embodiments, the polyvinyl alcohol-based film coating is Opadry® AMB II (e.g., Opadry® AMB II 88A620004 Yellow, Opadry® AMB II 88A220061 Yellow, Opadry® AMB II 88A170010 Beige).

In some embodiments, the polyvinyl alcohol-based film coating comprises poly(vinyl alcohol), macrogol (also known as polyethylene glycol (PEG)), titanium dioxide, and talc. In some embodiments, the polyvinyl alcohol-based film coating further comprises iron oxides. In some embodiments, the polyvinyl alcohol-based film coating is Opadry® II 85F.

In some embodiments, the coating is a hypromellose-based film coating. In some embodiments, the hypromellose-based film coating comprises hypromellose, macrogol (also known as polyethylene glycol (PEG)) and talc. In some embodiments, the hypromellose-based film coating further comprises iron oxides. In some embodiments, the hypromellose-based film coating is Opadry® 32F.

In some embodiments, the pharmaceutical composition is substantially free of Compound II, having the following structure:

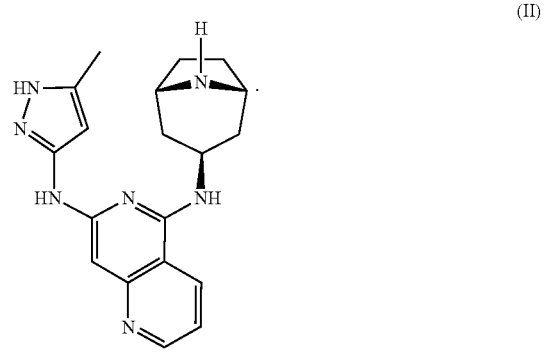 [SMILES: Cc1cc(Nc2cc3ncccc3c(N[C@@H]3C[C@H]4CC[C@@H](C3)N4)n2)n[nH]1]

(II)

In some embodiments, the pharmaceutical composition is substantially free of Compound III having the following structure:

(III)

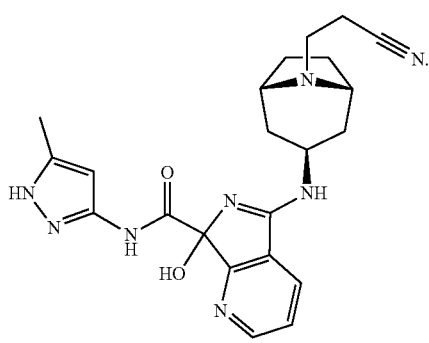

In some embodiments, the pharmaceutical composition is substantially free of Compound IV, having the following structure:

(IV)

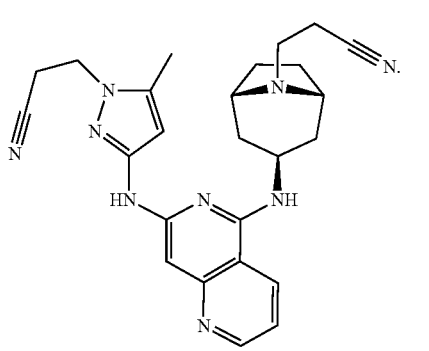

In some embodiments, the pharmaceutical composition is substantially free of acrylonitrile.

In some embodiments, the pharmaceutical composition exhibits at least 75% dissolution after 45 minutes in an aqueous solution having a pH of from 1 to 5.5. In some embodiments, the aqueous solution has a pH from 1 to 5. In some embodiments, the aqueous solution has a pH from 1 to 4.5. In some embodiments, the pharmaceutical composition exhibits at least 75% dissolution after 30 minutes in the aqueous solution. In some embodiments, the pharmaceutical composition exhibits at least 75% dissolution after 15 minutes in the aqueous solution. In some embodiments, the pharmaceutical composition exhibits at least 85% dissolution after 15 minutes in the aqueous solution. In some embodiments, the aqueous solution is at a temperature of about 37° C. In some embodiments, dissolution is assessed using a United States Pharmacopeia (USP) paddle method at 75 RPM. In some embodiments, dissolution is assessed using a United States Pharmacopeia (USP) paddle method at 75 RPM with a sinker.

In some embodiments, dissolution is assessed using a United States Pharmacopeia (USP) paddle method at 50 RPM to 75 RPM with or without a sinker. In some embodiments, dissolution is assessed using a United States Pharmacopeia (USP) paddle method at 50 RPM without a sinker. In some embodiments, dissolution is assessed using a United States Pharmacopeia (USP) paddle method at 60 RPM without a sinker. In some embodiments, dissolution is assessed using a United States Pharmacopeia (USP) paddle method at 75 RPM without a sinker. In some embodiments, dissolution is assessed using a United States Pharmacopeia (USP) paddle method at 50 RPM with a sinker. In some embodiments, dissolution is assessed using a United States Pharmacopeia (USP) paddle method at 60 RPM with a sinker. In some embodiments, dissolution is assessed using a United States Pharmacopeia (USP) paddle method at 75 RPM with a sinker.

In some embodiments, Compound I is present in an amount of about 20 mg. In some embodiments, the pharmaceutical composition comprises about 20 mg of Compound I; about 41.5 mg microcrystalline cellulose; about 30.5 mg lactose; about 1.0 mg hydrophobic colloidal silicon dioxide; about 3.0 mg magnesium stearate; about 4.0 mg L-HPC (e.g., LH-21); and a coating. In some embodiments, the pharmaceutical composition comprises 20 mg of Compound I; 41.5 mg microcrystalline cellulose; 30.5 mg lactose; 1.0 mg hydrophobic colloidal silicon dioxide; 3.0 mg magnesium stearate; 4.0 mg L-HPC (e.g. LH-21); and a coating. In some embodiments, the pharmaceutical composition comprises about 20 mg of Compound I; about 41.5 mg microcrystalline cellulose; about 30.5 mg lactose monohydrate; about 1.0 mg hydrophobic colloidal silicon dioxide; about 3.0 mg magnesium stearate; about 4.0 mg L-HPC (e.g., LH-21); and a coating. In some embodiments, the pharmaceutical composition comprises 20 mg of Compound I; 41.5 mg microcrystalline cellulose; 30.5 mg lactose monohydrate; 1.0 mg hydrophobic colloidal silicon dioxide; 3.0 mg magnesium stearate; 4.0 mg L-HPC (e.g. LH-21); and a coating.

In some embodiments, Compound I is present in an amount of about 80 mg. In some embodiments, the pharmaceutical composition comprises about 80 mg of Compound I; about 166 mg microcrystalline cellulose; about 122 mg lactose; about 4.0 mg hydrophobic colloidal silicon dioxide; about 12.0 mg magnesium stearate; about 16.0 mg L-HPC (e.g., LH-21); and a coating. In some embodiments, the pharmaceutical composition comprises 80 mg of Compound I; 166 mg microcrystalline cellulose; 122 mg lactose; 4.0 mg hydrophobic colloidal silicon dioxide; 12.0 mg magnesium stearate; 16.0 mg L-HPC (e.g., LH-21); and a coating. In some embodiments, the pharmaceutical composition comprises about 80 mg of Compound I; about 166 mg microcrystalline cellulose; about 122 mg lactose monohydrate; about 4.0 mg hydrophobic colloidal silicon dioxide; about 12.0 mg magnesium stearate; about 16.0 mg L-HPC (e.g., LH-21); and a coating. In some embodiments, the pharmaceutical composition comprises 80 mg of Compound I; 166 mg microcrystalline cellulose; 122 mg lactose monohydrate; 4.0 mg hydrophobic colloidal silicon dioxide; 12.0 mg magnesium stearate; 16.0 mg L-HPC (e.g., LH-21); and a coating.

In some embodiments, Compound I is present in an amount of about 200 mg. In some embodiments, the pharmaceutical composition comprises about 200 mg of Compound I; about 415 mg microcrystalline cellulose; about 305 mg lactose; about 10 mg hydrophobic colloidal silicon dioxide; about 30 mg magnesium stearate; about 40 mg L-HPC (e.g., LH-21); and a coating. In some embodiments, the pharmaceutical composition comprises 200 mg of Compound I; 415 mg microcrystalline cellulose; 305 mg lactose; 10 mg hydrophobic colloidal silicon dioxide; 30 mg magnesium stearate; 40 mg L-HPC (e.g., LH-21); and a coating. In some embodiments, the pharmaceutical composition comprises about 200 mg of Compound I; about 415 mg microcrystalline cellulose; about 305 mg lactose monohydrate; about 10 mg hydrophobic colloidal silicon dioxide; about 30 mg magnesium stearate; about 40 mg L-HPC (e.g., LH-21); and a coating. In some embodiments, the pharmaceutical composition comprises 200 mg of Compound I; 415 mg microcrystalline cellulose; 305 mg lactose monohydrate; 10 mg hydrophobic colloidal silicon dioxide; 30 mg magnesium stearate; 40 mg L-HPC (e.g., LH-21); and a coating.

In some embodiments, Compound I is locally acting in the gastrointestinal tract.

In some embodiments, the pharmaceutical composition is a tablet or capsule. In some embodiments, the pharmaceutical composition is a tablet. In some embodiments, the tablet is an immediate release tablet.

The present disclosure also provides a method of treating a gastrointestinal inflammatory disease comprising administering to a mammal in need thereof a therapeutically-effective amount of a pharmaceutical composition disclosed herein.

In some embodiments, the gastrointestinal inflammatory disease is inflammatory bowel disease. In some embodiments, the gastrointestinal inflammatory disease is ulcerative colitis. In some embodiments, the gastrointestinal inflammatory disease is Crohn's disease. In some embodiments, the pharmaceutical composition is administered once daily. In some embodiments, the mammal is a human.

The present disclosure also provides a method of preparing the pharmaceutical composition of the disclosure, the method comprising: (a) blending Compound I and hydrophobic colloidal silicon dioxide together to form a first mixture; (b) blending microcrystalline cellulose, lactose monohydrate, and L-HPC together with the first mixture to form a second mixture; (c) blending magnesium stearate together with the second mixture to form a third mixture; and (d) compressing the third mixture to form a tablet. In some embodiments, the hydrophobic colloidal silicon dioxide and Compound I are blended together via high shear mixing. In some embodiments, the hydrophobic colloidal silicon dioxide and Compound I are blended together via low shear mixing. In some embodiments, the method further comprises spraying the tablet with a fourth mixture comprising the coating and water.

DETAILED DESCRIPTION

Figure 1:
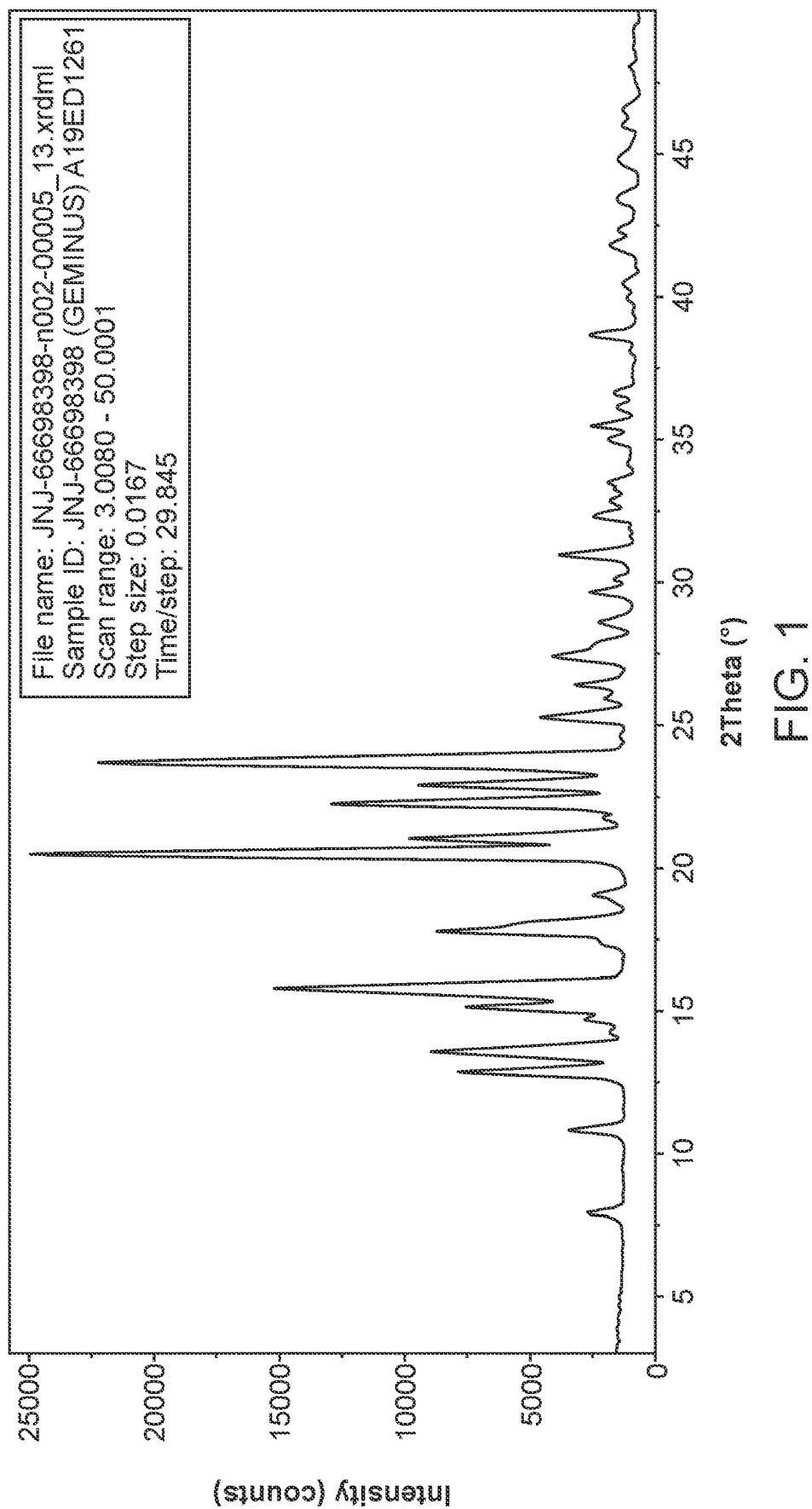
FIG. 1 is an XRPD diffractogram of Compound I.

Disclosed herein are formulations comprising 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile (Compound I):

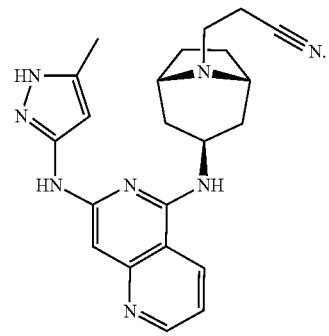 [SMILES: Cc1cc(Nc2cc3ncccc3c(N[C@@H]3C[C@H]4CC[C@@H](C3)N4CCC#N)n2)n[nH]1]

In some embodiments, the formulation comprises: about 20 wt % of Compound I; about 41.5 wt % microcrystalline cellulose; about 30.5 wt % lactose; about 1.0 wt % hydrophobic colloidal silicon dioxide; about 3.0 wt % magnesium stearate; about 4.0 wt % low-substituted hydroxypropyl cellulose; and optionally a coating. In some embodiments, the formulation comprises: about 20 wt % of Compound I; about 41.5 wt % microcrystalline cellulose; about 30.5 wt % lactose monohydrate; about 1.0 wt % hydrophobic colloidal silicon dioxide; about 3.0 wt % magnesium stearate; about 4.0 wt % low-substituted hydroxypropyl cellulose; and optionally a coating. In some embodiments, Compound I exhibits a purity of at least 99% as measured by UH PLC assay.

Definitions

It is to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to "an excipient" includes a combination of two or more such excipients, reference to "a glidant" includes one or more glidants, or mixtures of glidants, reference to "a filler" includes one or more fillers, or mixtures of fillers, and the like. Unless specifically stated or obvious from context, as used herein, the term "or" is understood to be inclusive and covers both "or" and "and."

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features. Although the open-ended term "comprising," as a synonym of terms such as including, containing, or having, is used herein to describe and claim the invention, the present technology, or embodiments thereof, may alternatively be described using more limiting terms such as "consisting of" or "consisting essentially of" the recited ingredients.

As used herein, "colloidal silicon dioxide" is fumed silicon dioxide that is produced by flame hydrolysis (see also Cas. No. 7631-86-9).

As used herein, Aerosil® 200 (see also Cas. No. 112945-52-5) means hydrophilic colloidal silicon dioxide. Aerosil® 200 is available from Evonik Corporation. The compendial name according to USP/NF for Aerosil® 200 is colloidal silicon dioxide. Synonyms that have been used for Aerosil® 200 are fumed silica and colloidal silica. In some embodiments, the Aerosil® 200 has a specific surface area (BET) of 175 $m^2$/g to 225 $m^2$/g. In some embodiments, the Aerosil® 200 has a specific surface area (BET) of 200 $m^2$/g.

As used herein, Aerosil® R 972 (see also Cas. No. 68611-44-9) means hydrophobic colloidal silicon dioxide. Aerosil® R 972 is available from Evonik Corporation. The compendial name according to USP/NF for Aerosil® R 972 is hydrophobic colloidal silica. Synonyms that have been used for Aerosil® R 972 are hydrophobic fumed silica, colloidal silicon dioxide aftertreated with dimethyldichlorosilane, and fumed silica aftertreated with dimethyldichlorosilane (DDS). In some embodiments, the Aerosil® R 972 has a specific surface area (BET) of 90 $m^2$/g to 130 $m^2$/g.

As used herein, silica and silicon dioxide are used interchangeably.

As used herein, BET (Brunauer-Emmett-Teller) surface area analysis measures specific surface area of a solid or porous material based on gas adsorption. The BET equation is known in the art.

Unless specifically stated or obvious from context, as used herein, the term "substantially" is understood as within a narrow range of variation or otherwise normal tolerance in the art. Substantially can be understood as within 5%, 4%, 3%, 2%, 1%, 0.5%, 0.1%, 0.05%, 0.01% or 0.001% of the stated value.

As used herein "substantially free of" refers to a compound of the disclosure or a composition comprising a compound of the disclosure containing no significant amount of such other crystalline or amorphous solid forms identified herein. For example, a composition of the disclosure can be substantially free of a given impurity when the composition constitutes no more than about 5% by weight of the impurity, or no more than about 4%, 3%, 2%, 1%, or no more than about 0.5% by weight of the impurity.

As used herein, the phrase "substantially as depicted in" when used in reference to graphical data in an identified figure refer to said identified figure, optionally having one or more of small variations, e.g., one or more variations described below or known to one of skill in the art. Such data may include, without limitation, X-ray powder diffractograms, differential scanning calorimetry curves, and thermogravimetric analysis curves, among others. As known in the art, such graphical data may provide additional technical information to further define the crystal polymorph, amorphous solid form, or other composition. As is understood by one of skill in the art, such graphical representations of data may be subject to small variations, e.g., in peak relative intensities and peak positions due to factors such as variations in instrument response and variations in sample concentration and purity. Nonetheless, one of skill in the art will readily be capable of comparing the graphical data in the figures herein with graphical data generated for a crystal polymorph, amorphous solid form, or other composition and confirm whether the two sets of graphical data are characterizing the same material or two different materials.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

"Coating" refers to a layer of material that is applied to the outer surface of a dosage form. A coating can comprise a sugar or polymer material, e.g., in a sugar coating, film coating, or enteric coating. A coating may confer specific benefits over uncoated dosage forms. For example, a coating may be used for a dosage form to achieve taste masking, odor masking, physical and chemical protection, e.g., protecting the drug in the stomach, and to control its release profile. Alternately, a coating may also be used to control the appearance of the dosage form (e.g., for marketing or patient compliance purposes).

"Colon" refers to the portion of the intestinal tract following the small intestine, and includes the ascending colon, transverse colon, descending colon, and the sigmoid colon.

"Gastrointestinal inflammatory disease", "inflammatory bowel disease" and "IBD" are used interchangeably to describe inflammatory diseases of the colon and small intestine. These inflammatory diseases include ulcerative colitis (including proctosigmoiditis, ulcerative proctitis, left-sided colitis, pancolitis, extensive colitis), Crohn's disease, collagenous colitis, lymphocytic colitis, diversion colitis, Behcet's disease, celiac disease, checkpoint cancer treatment-induced colitis, (e.g. CTLA-4 inhibitor-induced colitis), ileitis, graft versus host disease-related colitis, infectious colitis and other gastrointestinal diseases characterized by inflammation of the intestine and colon.

"Subject" refers to any animal, such as a mammal, including a human. The term "mammal" as used herein, encompasses any mammal. Examples of mammals include, but are not limited to, cows, horses, sheep, pigs, cats, dogs, mice, rats, rabbits, guinea pigs, non-human primates (NHPs) such as monkeys or apes, humans, etc., including a human.

"Therapeutically-effective amount" or "effective amount" refers to an amount that is effective to elicit the desired biological or medical response, including the amount of a compound that, when administered to a subject for treating a disease, is sufficient to effect such treatment for the disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (such as additive or synergistic effects) of the compounds.

As used herein, the term "treatment" or "treating," is defined as the application or administration of a therapeutic agent or a pharmaceutical composition, to a patient, or application or administration of a therapeutic agent or pharmaceutical composition to an isolated tissue or cell line from a patient (e.g., for diagnosis or ex vivo applications), who has a gastrointestinal inflammatory disorder. Such treatments may be specifically tailored or modified, based on knowledge obtained from the field of pharmacogenomics.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "D10" or "Dv10" means the particle diameter corresponding to 10% of the cumulative undersize distribution (by volume).

As used herein, the term "D50" or "Dv50" means the particle diameter corresponding to 50% of the cumulative undersize distribution (by volume).

As used herein, the term "D90" or "Dv90" means the particle diameter corresponding to 90% of the cumulative undersize distribution (by volume).

The present disclosure also includes salt forms of the compounds described herein. Examples of salts (or salt forms) include, but are not limited to, mineral or organic acid salts of basic residues such as amines, alkali or organic salts of acidic residues such as carboxylic acids, and the like. Lists of suitable salts are found in Remington's Pharmaceutical Sciences, 17th ed., Mack Publishing Company, Easton, Pa., 1985, p. 1418, the disclosure of which is hereby incorporated by reference in its entirety.

Formulations

As discussed in U.S. Pat. Nos. 9,725,470 and 10,072,026, (3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile) is a potent pan-JAK inhibitor that may have clinical potential in an inflammatory bowel disease (e.g., ulcerative colitis and Crohn's disease). This compound has the following formula (see, e.g., U.S. Pat. No. 9,725,470), and is also referred to herein as Compound I:

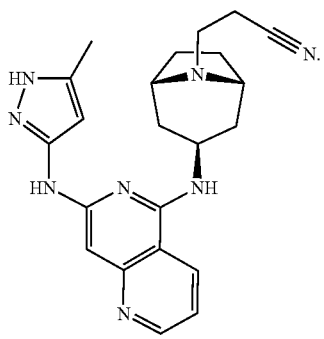 [SMILES: Cc1cc(Nc2cc3ncccc3c(N[C@@H]3C[C@H]4CC[C@@H](C3)N4CCC#N)n2)n[nH]1]

Disclosed herein are pharmaceutical compositions comprising Compound I that exhibit improved properties. For example, though Compound I is prone to decomposition in the presence of certain excipients, the pharmaceutical compositions described herein exhibit high chemical stability and minimal degradation of the active pharmaceutical ingredient (i.e., Compound I). Such improved stability could have a potentially beneficial impact on the manufacture of said pharmaceutical compositions, such as, for example, offering the ability to store process intermediates and the finished product for extended periods of time. Further, the pharmaceutical compositions described herein are immediate-release formulations highly soluble in stomach pH and locally acting on the gastrointestinal tract. Accordingly, the formulations described herein exhibit low systemic exposure. In some embodiments, the formulations described herein may also potentially result in an improvement of the quality of Compound I. In some embodiments, the formulations described herein may also exhibit improved pharmacokinetic properties and/or potentially improved bioavailability.

In some embodiments, the disclosure provides a pharmaceutical composition comprising Compound I, or a pharmaceutically acceptable salt thereof; one or more fillers; one or more glidants; one or more lubricants; one or more disintegrants; and optionally a coating.

Compound I can exhibit a purity of at least 93%, or a purity of at least 94%, 95%, 96%, 97%, 98%, or a purity of at least 99%, as measured by Ultra High Performance Liquid Chromatography (UPLC or UHPLC) assay. In some embodiments, Compound I can exhibit a purity of at least 97% as measured by Ultra High Performance Liquid Chromatography (UHPLC) assay.

Compound I can exhibit a purity of at least 99%, or a purity of at least 99.1%, 99.2%, 99.3%, 99.4%, 99.5%, 99.6%, 99.7%, 99.8%, or a purity of at least 99.9%, as measured by UHPLC assay. In some embodiments, Compound I can exhibit a purity of at least 99.5% as measured by UHPLC assay.

The pharmaceutical composition can include Compound I in any suitable solid form, including amorphous, crystalline, or a combination thereof. For example, Compound I can exhibit any suitable crystalline form. Representative crystalline forms include one or more crystalline forms described in U.S. Pat. Nos. 9,725,470 and 10,072,026, each of which is incorporated herein in its entirety for all purposes.

In some embodiments, Compound I is characterized by an X-ray powder diffraction (XRPD) pattern comprising peaks expressed in degrees-2-theta at angles (±0.20) of 7.82, 12.82, 15.76, and 20.51.

In some embodiments, Compound I is characterized by an X-ray powder diffraction (XRPD) pattern comprising peaks expressed in degrees-2-theta at angles (±0.20) of 7.82, 10.75, 12.82, 13.41, 13.59, 14.62, 15.08, 15.50, 15.76, 17.68, 20.51, 20.99, 22.18, 22.87, and 23.73.

In some embodiments, Compound I is characterized by an X-ray powder diffraction (XRPD) pattern comprising peaks substantially as depicted in FIG. 1.

In some embodiments, Compound I is characterized by an X-ray powder diffraction (XRPD) pattern comprising peaks expressed in degrees-2-theta at angles (±0.20) of 7.88, 12.85, 15.80, and 20.41.

In some embodiments, Compound I is characterized by an X-ray powder diffraction (XRPD) pattern comprising peaks expressed in degrees-2-theta at angles (±0.20) of 7.88, 10.80, 12.85, 13.46, 13.65, 14.65, 15.10, 15.55, 15.80, 17.72, 20.41, 21.00, 22.26, 22.93, and 23.65.

Figure 4:
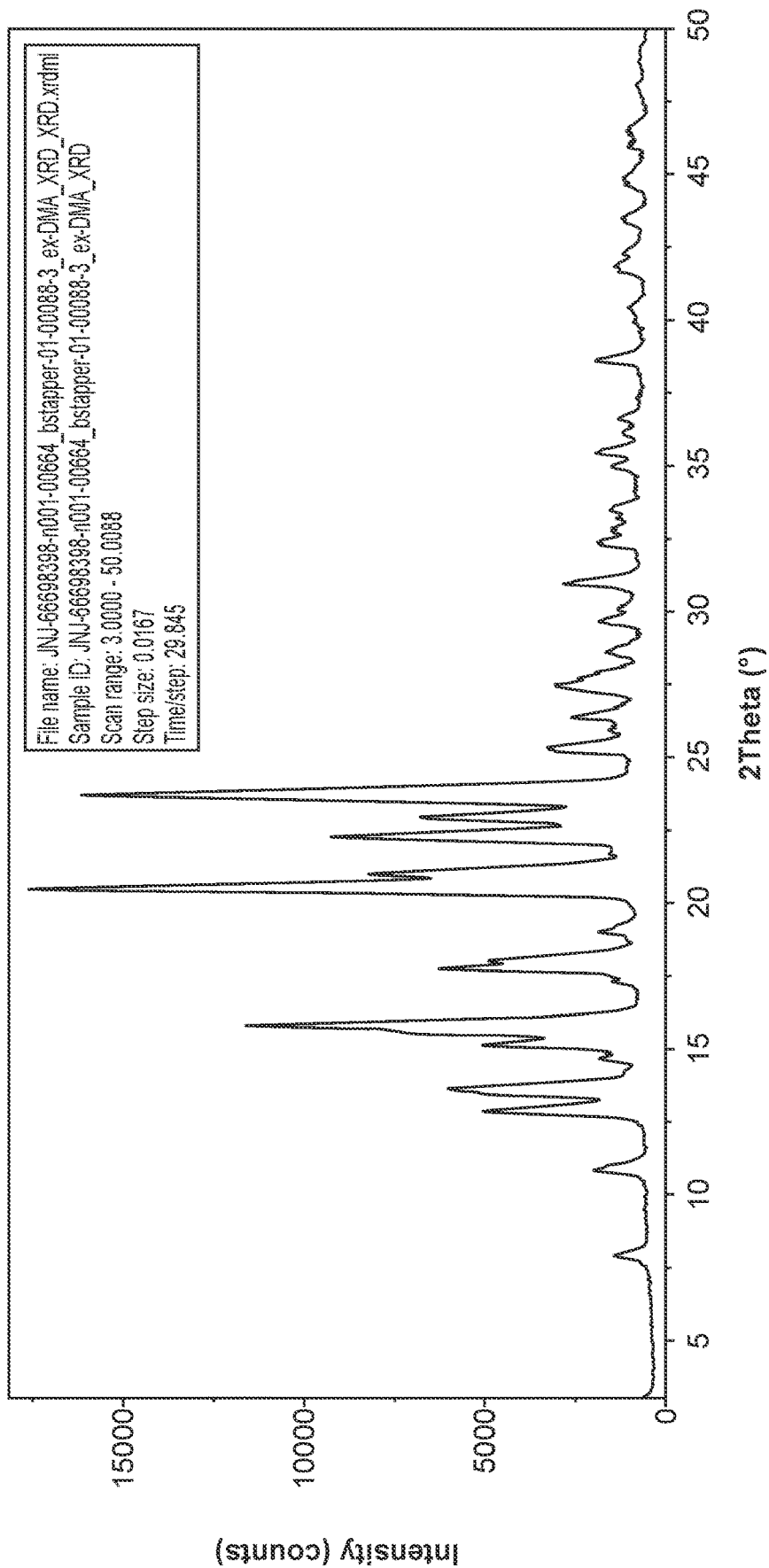
FIG. 4 is an XRPD diffractogram of Compound I.

In some embodiments, Compound I is characterized by an X-ray powder diffraction (XRPD) pattern comprising peaks substantially as depicted in FIG. 4.

In some embodiments, Compound I is characterized by an X-ray powder diffraction (XRPD) pattern comprising peaks expressed in degree-2-theta at angles (±0.20) of 7.87, 12.78, 15.78, and 20.41.

In some embodiments, Compound I is characterized by an X-ray powder diffraction (XRPD) pattern comprising peaks expressed in degree-2-theta at angles (±0.20) of 7.87, 10.80, 12.78, 13.47, 13.64, 14.66, 15.11, 15.54, 15.78, 17.75, 20.41, 21.00, 22.22, 22.93, and 23.65.

In some embodiments, Compound I is in a crystalline form characterized by substantially uniform particle size. In some embodiments, the crystalline form of Compound I has a Dv50 particle size of about 18 μm to about 28 μm, as determined by static image analysis. In some embodiments, the crystalline form of Compound I has a Dv50 particle size of about 20 μm to about 26 μm, as determined by static image analysis. In some embodiments, the crystalline form of Compound I has a Dv50 particle size of about 11 μm to about 17 μm, as determined by dry dispersion laser diffraction. In some embodiments, the crystalline form of Compound I has a Dv50 particle size of about 13 μm to about 15 μm, as determined by dry dispersion laser diffraction.

In some embodiments, the crystalline form of Compound I has a Dv50 particle size of about 59 μm to about 69 μm, as determined by static image analysis. In some embodiments, the crystalline form of Compound I has a Dv50 particle size of about 61 μm to about 67 μm, as determined by static image analysis. In some embodiments, the crystalline form of Compound I has a Dv50 particle size of about 63 μm to about 65 μm, as determined by static image analysis.

In some embodiments, the crystalline form of Compound I has a Dv50 particle size of about 110 μm to about 120 μm, as determined by static image analysis. In some embodiments, the crystalline form of Compound I has a Dv50 particle size of about 112 μm to about 118 μm, as determined by static image analysis. In some embodiments, the crystalline form of Compound I has a Dv50 particle size of about 115 μm to about 117 μm, as determined by static image analysis. In some embodiments, the crystalline form of Compound I has a Dv50 particle size of about 70 μm to about 80 μm, as determined by dry dispersion laser diffraction. In some embodiments, the crystalline form of Compound I has a Dv50 particle size of about 72 μm to about 78 μm, as determined by dry dispersion laser diffraction. In some embodiments, the crystalline form of the compound of Formula (VIII) has a particle size (Dv50) of about 75 μm, as determined by dry dispersion laser diffraction.

In some embodiments, Compound I is locally acting in the gastrointestinal tract.

Fillers or diluents for use in the formulations of the disclosure include fillers or diluents typically used in the formulation of pharmaceuticals. Examples of fillers or diluents for use in accordance with the disclosure include, but are not limited to, sugars such as lactose (e.g., anhydrous lactose, directly compressible anhydrous lactose, lactose monohydrate, modified lactose monohydrate), dextrose, glucose, sucrose, cellulose, starches and carbohydrate derivatives, polysaccharides (including dextrates and maltodextrin), polyols (including mannitol, xylitol, and sorbitol), cyclodextrins, calcium carbonates, magnesium carbonates, microcrystalline cellulose, combinations thereof, and the like. In some embodiments the filler or diluent is lactose, microcrystalline cellulose, or a combination thereof.

Glidants or anti-adherents for use in the formulations of the disclosure include glidants or anti-adherents typically used in the formulation of pharmaceuticals. Examples of glidants or anti-adherents suitable for use in accordance with the disclosure include but are not limited to talc, silicon dioxide, and magnesium stearate. In some embodiments, the glidant or anti-adherent is hydrophobic colloidal silicon dioxide.

Lubricants for use in the formulations of the disclosure include lubricants commonly used in the formulation of pharmaceuticals. Examples of lubricants for use in the present disclosure include, but are not limited to magnesium carbonate, calcium silicate, talc, magnesium stearate, sodium stearyl fumarate, calcium stearate, stearic acid, sodium stearyl fumarate, polyethylene glycol, sodium lauryl sulphate, magnesium lauryl sulphate, sodium benzoate, colloidal silicon dioxide, fumed silicon dioxide, magnesium oxide, mineral oil, waxes, glyceryl behenate, polyethylene glycol, combinations thereof, and the like. In some embodiments, the lubricant is sodium stearyl fumarate. In some embodiments, the lubricant is magnesium stearate.

Disintegrants for use in the formulations of the present invention include disintegrants commonly used in the formulation of pharmaceuticals. Examples of disintegrants for use in the present invention include, but are not limited to, starches, clays, celluloses, alginates and gums and cross-linked starches, celluloses and polymers, combinations thereof and the like. Representative disintegrants include low-substituted hydroxypropylcellulose (L-HPC), microcrystalline cellulose, croscarmellose sodium, alginic acid, sodium alginate, crospovidone, cellulose, agar and related gums, corn starch, potato starch, sodium starch glycolate, Veegum® HV (magnesium aluminum silicate), methylcellulose, agar, bentonite, carboxymethylcellulose, alginic acid, guar gum combinations thereof, and the like. In some embodiments, the disintegrant is low-substituted hydroxypropylcellulose (L-HPC).

When present, any suitable coating can be used in the pharmaceutical compositions described herein. In some embodiments, the coating provides cosmetic benefits to the pharmaceutical composition. In some embodiments, the coating helps to protect the pharmaceutical composition. Coatings may comprise multiple components, including, by non-limiting example, plasticizers, waxes, opacifying agents, and colorants. In some embodiments the coating comprises one or more components from among the following: poly(vinyl alcohol), glycerol monocaprylocaprate type I and sodium lauryl sulfate, talc, titanium dioxide, macrogol (also called polyethylene glycol), lecithin, Brilliant Blue FCF, indigo carmine, iron oxide yellow, iron oxide red, black iron oxide, hypromellose, lactose monohydrate, hydroxypropyl methylcellulose, polydextrose, triacetin, carnauba wax, glycerin diethyl phthalate, dibutyl sebacate, and triethyl citrate. Certain coatings suitable for use in the pharmaceutical compositions disclosed herein comprise poly(vinyl alcohol), glycerol monocaprylocaprate type I and sodium lauryl sulfate and optionally further comprise talc, titanium dioxide, polyethylene glycol, lecithin, Brilliant Blue FCF, indigo carmine, hypromellose, lactose monohydrate, iron oxide yellow, iron oxide red, or black iron oxide.

The pharmaceutical composition of the disclosure can also include a protective outer layer (e.g., a coating). The protective outer layer of the pharmaceutical composition can include from about 10% to about 95% of polymer based on the weight of the coating layer, and can be prepared employing conventional procedures. For example, the protective outer layer of the pharmaceutical composition may include from about 20% to about 90% of polymer based on the weight of the coating layer. The formulation can contain at least one coating layer polymer and a coating solvent, for example, water, which is used for processing and removed by drying. Suitable examples of polymers for the coating layer include, but are not limited to, hydroxypropyl methylcellulose, polyvinyl alcohol (PVA), ethyl cellulose, methacrylic polymers, hydroxypropyl cellulose, and starch.

The pharmaceutical compositions of the disclosure can also comprise additional excipients, including surfactants, polymers, binders, antioxidants, and chelating agents. Surfactants suitable for use in the formulations of the disclosure include surfactants commonly used in the formulation of pharmaceuticals. Examples of surfactants include, but are not limited to, ionic- and nonionic surfactants or wetting agents commonly used in the formulation of pharmaceuticals, such as ethoxylated castor oil, polyglycolyzed glycerides, acetylated monoglycerides, sorbitan fatty acid esters, poloxamers, polyoxyethylene sorbitan fatty acid esters, polyoxyethylene derivatives, monoglycerides or ethoxylated derivatives thereof, diglycerides or polyoxyethylene derivatives thereof, sodium docusate, sodium laurylsulfate, cholic acid or derivatives thereof, lecithins, phospholipids, combinations thereof, and the like.

Binders for use in the formulations of the present disclosure include binders commonly used in the formulation of pharmaceuticals. Examples of binders include but are not limited to cellulose derivatives (including hydroxypropyl cellulose, hydroxypropyl methylcellulose, methylcellulose, and sodium carboxymethyl cellulose), glycol, sucrose, dextrose, corn syrup, polysaccharides (including acacia, tragacanth, guar, alginates and starch), corn starch, pregelatinized starch, modified corn starch, gelatin, polyvinylpyrrolidone, polyethylene, polyethylene glycol, combinations thereof and the like.

Antioxidants and chelating agents suitable for use in the formulations of the disclosure include butylated hydroxyanisole (BHA), butylated hydroxytoluene (BHT), propyl gallate (PG), sodium metabisulfite, ascorbyl palmitate, potassium metabisulfite, disodium EDTA (ethylenediamine tetraacetic acid; also known as disodium edentate), EDTA, tartaric acid, citric acid, citric acid monohydrate, and sodium sulfite.

In some embodiments, the disclosure provides a pharmaceutical composition comprising Compound I:

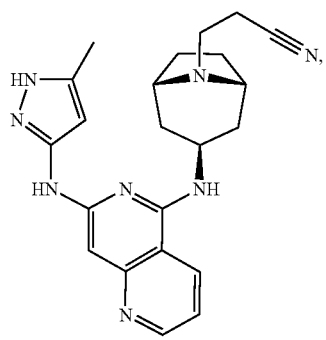 [SMILES: Cc1cc(Nc2cc3ncccc3c(N[C@@H]3C[C@H]4CC[C@@H](C3)N4CCC#N)n2)n[nH]1]

or a pharmaceutically acceptable salt thereof; microcrystalline cellulose; lactose; silicon dioxide (e.g., hydrophobic colloidal silicon dioxide); magnesium stearate; a disintegrant (e.g., low-substituted hydroxypropyl cellulose (L-HPC)); and optionally a coating.

In some embodiments, the disclosure provides a pharmaceutical composition comprising Compound I:

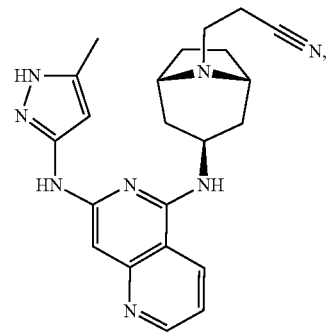 [SMILES: Cc1cc(Nc2cc3ncccc3c(N[C@@H]3C[C@H]4CC[C@@H](C3)N4CCC#N)n2)n[nH]1]

or a pharmaceutically acceptable salt thereof; microcrystalline cellulose; lactose monohydrate; silicon dioxide (e.g., hydrophobic colloidal silicon dioxide); magnesium stearate; a disintegrant (e.g., low-substituted hydroxypropyl cellulose (L-HPC)); and optionally a coating.

In some embodiments, the pharmaceutical composition comprises about 10 wt % to about 30 wt % of Compound I, or a pharmaceutically acceptable salt thereof. In some embodiments, the pharmaceutical composition comprises about 15 wt % to about 25 wt % of Compound I, or a pharmaceutically acceptable salt thereof. In some embodiments, the pharmaceutical composition comprises about 20 wt % of Compound I, or a pharmaceutically acceptable salt thereof. In some embodiments, the pharmaceutical composition comprises 20 wt % of Compound I, or a pharmaceutically acceptable salt thereof.

In some embodiments, the pharmaceutical composition comprises about 31.5 wt % to about 51.5 wt % microcrystalline cellulose. In some embodiments, the pharmaceutical composition comprises about 36.5 wt % to about 46.5 wt % microcrystalline cellulose. In some embodiments, the pharmaceutical composition comprises about 41.5 wt % microcrystalline cellulose. In some embodiments, the pharmaceutical composition comprises 41.5 wt % microcrystalline cellulose.

In some embodiments, the pharmaceutical composition comprises about 20.5 wt % to about 40.5 wt % lactose. In some embodiments, the pharmaceutical composition comprises about 25.5 wt % to about 35.5 wt % lactose. In some embodiments, the pharmaceutical composition comprises about 30.5 wt % lactose. In some embodiments, the pharmaceutical composition comprises 30.5 wt % lactose.

In some embodiments, the pharmaceutical composition comprises about 20.5 wt % to about 40.5 wt % lactose monohydrate. In some embodiments, the pharmaceutical composition comprises about 25.5 wt % to about 35.5 wt % lactose monohydrate. In some embodiments, the pharmaceutical composition comprises about 30.5 wt % lactose monohydrate. In some embodiments, the pharmaceutical composition comprises 30.5 wt % lactose monohydrate.

In some embodiments, the pharmaceutical composition comprises about 0.5 wt % to about 1.5 wt % hydrophobic colloidal silicon dioxide. In some embodiments, the pharmaceutical composition comprises about 1.0 wt % hydrophobic colloidal silicon dioxide. In some embodiments, the pharmaceutical composition comprises 1.0 wt % hydrophobic colloidal silicon dioxide.

In some embodiments, the pharmaceutical composition comprises about 0.5 wt % to about 6.5 wt % magnesium stearate. In some embodiments, the pharmaceutical composition comprises about 2 wt % to about 4 wt % magnesium stearate. In some embodiments, the pharmaceutical composition comprises about 3 wt % magnesium stearate. In some embodiments, the pharmaceutical composition comprises 3 wt % magnesium stearate.

In some embodiments, the pharmaceutical composition comprises about 0.5 wt % to about 7.5 wt % L-HPC. In some embodiments, the pharmaceutical composition comprises about 4.0 wt % L-HPC. In some embodiments, the pharmaceutical composition comprises 4.0 wt % L-HPC.

In some embodiments, the coating is present in an amount from about 0% to about 10% by weight of the pharmaceutical composition. In some embodiments, the coating is present in an amount from about 0% to about 6% by weight of the pharmaceutical composition. In some embodiments, the coating is present in an amount from about 3% to about 5% by weight of the pharmaceutical composition. In some embodiments, the coating is present in an amount of about 4% by weight of the pharmaceutical composition.

In some embodiments, the pharmaceutical composition comprises about 10 wt % to about 30 wt % of Compound I, or a pharmaceutically acceptable salt thereof; about 31.5 wt % to about 51.5 wt % microcrystalline cellulose; about 20.5 wt % to about 40.5 wt % lactose; about 0.5 wt % to about 1.5 wt % hydrophobic colloidal silicon dioxide; about 0.5 wt % to about 6.5 wt % magnesium stearate; about 0.5 wt % to about 7.5 wt % L-HPC; and optionally a coating.

In some embodiments, the pharmaceutical composition comprises about 20 wt % of the compound of Formula (I), or a pharmaceutically acceptable salt thereof; about 41.5 wt % microcrystalline cellulose; about 30.5 wt % lactose; about 1.0 wt % hydrophobic colloidal silicon dioxide; about 3.0 wt % magnesium stearate; about 4.0 wt % L-HPC; and optionally a coating.

In some embodiments, the pharmaceutical composition comprises 20 wt % of the compound of Formula (I), or a pharmaceutically acceptable salt thereof; 41.5 wt % microcrystalline cellulose; 30.5 wt % lactose; 1.0 wt % hydrophobic colloidal silicon dioxide; 3.0 wt % magnesium stearate; 4.0 wt % L-HPC; and optionally a coating.

In some embodiments, the pharmaceutical composition comprises about 10 wt % to about 30 wt % of Compound I, or a pharmaceutically acceptable salt thereof; about 31.5 wt % to about 51.5 wt % microcrystalline cellulose; about 20.5 wt % to about 40.5 wt % lactose monohydrate; about 0.5 wt % to about 1.5 wt % hydrophobic colloidal silicon dioxide; about 0.5 wt % to about 6.5 wt % magnesium stearate; about 0.5 wt % to about 7.5 wt % L-HPC; and optionally a coating.

In some embodiments, the pharmaceutical composition comprises about 20 wt % of the compound of Formula (I), or a pharmaceutically acceptable salt thereof; about 41.5 wt % microcrystalline cellulose; about 30.5 wt % lactose monohydrate; about 1.0 wt % hydrophobic colloidal silicon dioxide; about 3.0 wt % magnesium stearate; about 4.0 wt % L-HPC; and optionally a coating.

In some embodiments, the pharmaceutical composition comprises 20 wt % of the compound of Formula (I), or a pharmaceutically acceptable salt thereof; 41.5 wt % microcrystalline cellulose; 30.5 wt % lactose monohydrate; 1.0 wt % hydrophobic colloidal silicon dioxide; 3.0 wt % magnesium stearate; 4.0 wt % L-HPC; and optionally a coating.

Any suitable form of microcrystalline cellulose can be used in the pharmaceutical compositions described herein. Certain forms of microcrystalline cellulose include partially depolymerized alphacellulose and silicified microcrystalline cellulose. In some embodiments, the microcrystalline cellulose is partially depolymerized alphacellulose. Varying grades of microcrystalline cellulose are suitable for use in the pharmaceutical compositions described herein. Accordingly, the pharmaceutical compositions of the disclosure may comprise microcrystalline cellulose having varying nominal particle sizes, varying bulk densities, varying degrees of polymerization (DP), and varying percentages of loss on drying (LOD). In some embodiments, the microcrystalline cellulose has a nominal particle size from about 90 µm to about 110 µm. In some embodiments, the microcrystalline cellulose has a nominal particle size of about 100 µm. In some embodiments, the microcrystalline cellulose has a bulk density ranging from about 0.28 g/mL to about 0.33 g/mL. In some embodiments, the microcrystalline cellulose has a degree of polymerization (DP) ranging from about 180 to about 285. In some embodiments, the microcrystalline cellulose has a percentage of loss on drying (LOD) ranging from about 3.0% to about 5.0%. Examples of microcrystalline cellulose suitable for use in the pharmaceutical compositions of the disclosure include Avicel™ types PH-101, PH-102, PH-103, PH-105, PH-112, PH-113, PH-200, PH-301. In some embodiments, the microcrystalline cellulose is an Avicel® microcrystalline cellulose. In some embodiments, the microcrystalline cellulose is Avicel® PH-102.

Any suitable form of lactose can be used in the pharmaceutical compositions described herein. For example, any suitable form of lactose monohydrate can be used in the pharmaceutical compositions described herein. Additionally, crystalline lactose, amorphous lactose, and mixtures thereof are suitable for use in the pharmaceutical compositions of the disclosure. In some embodiments, the lactose monohydrate is a spray-dried mixture of crystalline lactose monohydrate and amorphous lactose. In some embodiments, the lactose is Lactose 316 Fast-Floe (e.g., a spray-dried mixture of crystalline lactose monohydrate and amorphous lactose). In some embodiments, the lactose is SuperTab® SD11 (e.g., a spray-dried mixture of crystalline lactose monohydrate and amorphous lactose).

Any suitable form of silicon dioxide, i.e., silica, can be used in the formulations described herein. Certain forms of silicon dioxide suitable for use in the pharmaceutical compositions described herein include hydrophobic silicon dioxide, colloidal silicon dioxide, hydrophobic colloidal silicon dioxide, hydrophilic colloidal silicon dioxide, fumed silicon dioxide, and the like. In some embodiments, the silicon dioxide is hydrophobic silicon dioxide. In some embodiments, the silicon dioxide is hydrophobic colloidal silicon dioxide. In some embodiments, the silicon dioxide is colloidal silicon dioxide after-treated with dimethyldichlorosilane. In some embodiments, the silicon dioxide is an Aerosil® silicon dioxide. In some embodiments, the silicon dioxide is Aerosil® R972.

Any suitable form of magnesium stearate can be used in the pharmaceutical compositions described herein. Several types and grades of magnesium stearate are suitable for use in the disclosed pharmaceutical compositions. Accordingly, magnesium stearate having varying specific surface areas and varying median particle sizes can be used in the pharmaceutical compositions disclosed herein. In some embodiments, the magnesium stearate has a specific surface area of between about 6 m$^2$/g and about 10 m$^2$/g. In some embodiments, the magnesium stearate has a median particle size of between about 7 µm and about 11 µm. In some embodiments, the magnesium stearate has a specific surface area of between 6 and 10 m$^2$/g and a median particle size of between 7 and 11 µm. In some embodiments, the magnesium stearate is Ligamed® MF-2-V.

Preferably, the disintegrant of the pharmaceutical composition is low-substituted hydroxypropylcellulose (L-HPC). Several types and grades of L-HPC are suitable for use in the pharmaceutical compositions of the present disclosure. For example, L-HPC having varying hydroxypropoxy content and varying particle sizes may be used. In some embodiments, the L-HPC has about 7.0% to about 16.0% hydroxypropoxy content. In some embodiments, the L-HPC has about 7.0% to about 9.9% hydroxypropoxy content. In some embodiments, the L-HPC has about 10.0% to about 12.9% hydroxypropoxy content. In some embodiments, the L-HPC has about 13.0% to about 15.9% hydroxypropoxy content.

In some embodiments, the L-HPC has a Dv50 particle size from about 17 μm to about 65 μm. In some embodiments, the L-HPC has a Dv50 particle size from about 17 μm to about 23 μm. In some embodiments, the L-HPC has a Dv50 particle size from about 35 μm to about 55 μm. In some embodiments, the L-HPC has a Dv50 particle size from about 45 μm to about 65 μm.

In some embodiments, the L-HPC has a Dv90 particle size from about 40 μm to about 200 μm. In some embodiments, the L-HPC has a Dv90 particle size from about 70 μm to about 200 μm. In some embodiments, the L-HPC has a Dv90 particle size from about 150 μm to about 200 μm. In some embodiments, the L-HPC has a Dv90 particle size from about 100 μm to about 150 μm. In some embodiments, the L-HPC has a Dv90 particle size from about 70 μm to about 130 μm. In some embodiments, the L-HPC has a Dv90 particle size from about 40 μm to about 100 μm.

In some embodiments, the L-HPC has about 5.0% to about 16.0% hydroxypropoxy content and a Dv50 particle size from about 35 μm to about 55 μm. In some embodiments, the L-HPC has about 7.0% to about 15.9% hydroxypropoxy content and a Dv50 particle size from about 35 μm to about 55 μm. In some embodiments, the L-HPC has about 10.0% to about 12.9% hydroxypropoxy content and a Dv50 particle size from about 35 μm to about 55 μm. In some embodiments, the L-HPC has about 10.0% to about 12.9% hydroxypropoxy content; a Dv50 particle size from about 35 μm to about 55 μm; and a Dv90 particle size from about 100 μm to about 150 μm. In some embodiments, the L-HPC is L-HPC LH-21.

In some embodiments, the pharmaceutical composition comprises a coating.

When present, any suitable coating can be used in the pharmaceutical compositions described herein. Suitable coatings may comprise multiple components, including, by non-limiting example, plasticizers, waxes, opacifying agents, and colorants. In some embodiments, the coating comprises one or more components from among the following: poly(vinyl alcohol), glycerol monocaprylocaprate type I and sodium lauryl sulfate, talc, titanium dioxide, polyethylene glycol, lecithin, Brilliant Blue FCF, indigo carmine, iron oxide yellow, iron oxide red, black iron oxide, hydroxypropyl methylcellulose, polydextrose, triacetin, carnuba wax, glycerin diethyl phthalate, dibutyl sebacate, and triaethyl citrate.

In some embodiments, the coating is a polyvinyl alcohol-based film coating. In some embodiments, the polyvinyl alcohol-based film coating comprises poly(vinyl alcohol), glycerol monocaprylocaprate type I, titanium dioxide, and talc. In some embodiments, the polyvinyl alcohol-based film coating comprises poly(vinyl alcohol), glycerol monocaprylocaprate type I, titanium dioxide, talc, and sodium lauryl sulfate. In some embodiments, the polyvinyl alcohol-based film coating further comprises iron oxides. In some embodiments, the polyvinyl alcohol-based film coating is Opadry® AMB II (e.g., Opadry® AMB II 88A620004 Yellow, Opadry® AMB II 88A220061 Yellow, Opadry® AMB II 88A170010 Beige). In some embodiments, the coating is Opadry® AMB II 88A620004 Yellow. In some embodiments, the coating is Opadry® AMB II 88A220061 Yellow. In some embodiments, the coating is Opadry® AMB II 88A170010 Beige.

In some embodiments, the polyvinyl alcohol-based film coating comprises poly(vinyl alcohol), talc, titanium dioxide, iron oxide yellow, glycerol monocaprylocaprate type I, sodium lauryl sulfate, and iron oxide red (i.e., Opadry® AMB II 88A170010 Beige).

In some embodiments, the polyvinyl alcohol-based film coating comprises poly(vinyl alcohol), talc, titanium dioxide, iron oxide yellow, glycerol monocaprylocaprate type I, and sodium lauryl sulfate (i.e., Opadry® AMB II 88A220061 Yellow).

In some embodiments, the polyvinyl alcohol-based film coating comprises poly(vinyl alcohol), macrogol (also called polyethylene glycol), titanium dioxide, and talc. In some embodiments, the polyvinyl alcohol-based film coating further comprises iron oxides. In some embodiments, the polyvinyl alcohol-based film coating is Opadry® II 85F.

In some embodiments, the coating is a hypromellose-based film coating. In some embodiments, the hypromellose-based film coating comprises hypromellose, macrogol (also called polyethylene glycol) and talc. In some embodiments, the hypromellose-based film coating further comprises iron oxides. In some embodiments, the hypromellose-based film coating is Opadry® 32F.

The pharmaceutical compositions described herein exhibit high chemical stability, particularly with respect to Compound I. Notably, Compound I is susceptible to reverse Michael addition of the propionitrile group to afford the unsubstituted nortropane Compound II and acrylonitrile:

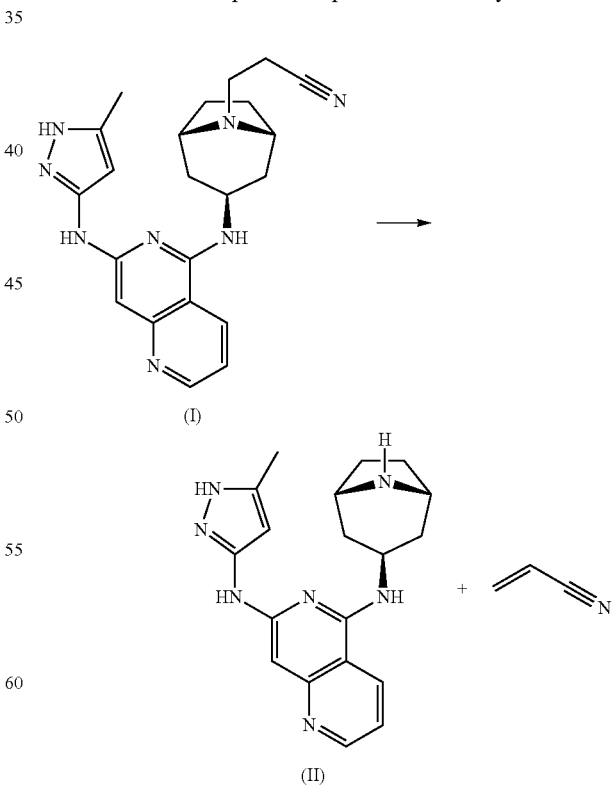

However, the pharmaceutical compositions of the present disclosure exhibit minimal decomposition of Compound I.

Accordingly, in some embodiments, the disclosure provides a pharmaceutical composition that is substantially free of impurities and/or degradation products. In some embodiments, the pharmaceutical composition comprises less than about 5% of total degradation products.

In some embodiments, the pharmaceutical composition is substantially free of Compound II, having the following structure:

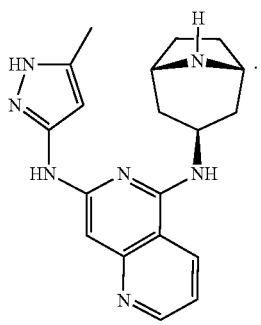

(II)

In some embodiments, the pharmaceutical composition comprises less than about 5% by weight of Compound II. In some embodiments, the pharmaceutical composition comprises less than about 4% by weight of Compound II. In some embodiments, the pharmaceutical composition comprises less than about 3% by weight of Compound II. In some embodiments, the pharmaceutical composition comprises less than about 2% by weight of Compound II.

In some embodiments, the pharmaceutical composition is substantially free of Compound III, having the following structure:

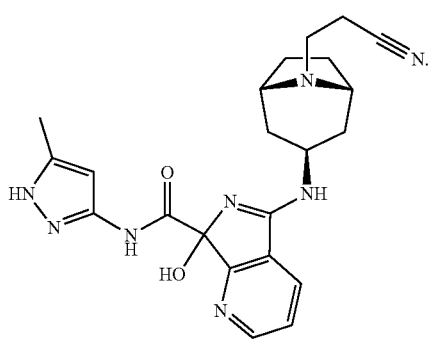

(III)

In some embodiments, the pharmaceutical composition comprises less than about 5% by weight of Compound III. In some embodiments, the pharmaceutical composition comprises less than about 4% by weight of Compound III. In some embodiments, the pharmaceutical composition comprises less than about 3% by weight of Compound III. In some embodiments, the pharmaceutical composition comprises less than about 2% by weight of Compound III.

In some embodiments, the pharmaceutical composition is substantially free of a Compound IV, having the following structure:

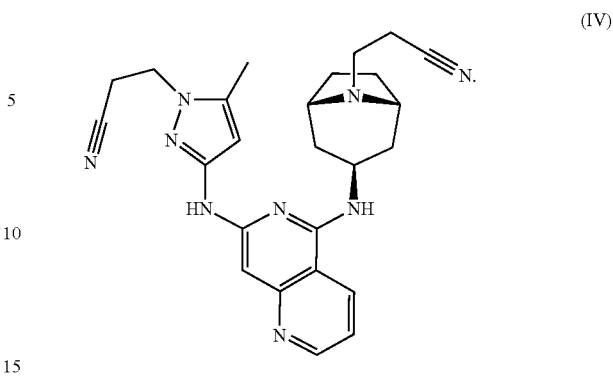

(IV)

In some embodiments, the pharmaceutical composition comprises less than about 5% by weight of Compound IV. In some embodiments, the pharmaceutical composition comprises less than about 4% by weight of Compound IV. In some embodiments, the pharmaceutical composition comprises less than about 3% by weight of Compound IV. In some embodiments, the pharmaceutical composition comprises less than about 2% by weight of Compound IV.

In some embodiments, the pharmaceutical composition is substantially free of any unspecified degradation product (e.g., any degradation product of Compound I that is not Compound II, Compound III, or Compound IV). In some embodiments, the pharmaceutical composition comprises less than about 3% by weight of any unspecified degradation product. In some embodiments, the pharmaceutical composition comprises less than about 2% by weight of any unspecified degradation product. In some embodiments, the pharmaceutical composition comprises less than about 1% by weight of any unspecified degradation product. In some embodiments, the pharmaceutical composition comprises less than about 0.5% by weight of any unspecified degradation product. In some embodiments, the pharmaceutical composition comprises less than about 0.3% by weight of any unspecified degradation product.

In some embodiments, the pharmaceutical composition is substantially free of acrylonitrile as measured by head space gas chromatography. In some embodiments, the pharmaceutical composition comprises less than about 400 ppm acrylonitrile. In some embodiments, the pharmaceutical composition comprises less than about 350 ppm acrylonitrile. In some embodiments, the pharmaceutical composition comprises less than about 300 ppm acrylonitrile. In some embodiments, the pharmaceutical composition comprises less than about 250 ppm acrylonitrile. In some embodiments, the pharmaceutical composition comprises less than about 200 ppm acrylonitrile. In some embodiments, the pharmaceutical composition comprises less than about 150 ppm acrylonitrile. In some embodiments, the pharmaceutical composition comprises less than about 75 ppm acrylonitrile. In some embodiments, the pharmaceutical composition comprises less than about 30 ppm acrylonitrile.

The pharmaceutical compositions described herein exhibit consistent and rapid dissolution profiles. In particular the pharmaceutical compositions of the present disclosure are capable of exhibiting at least 50% dissolution, 60% dissolution, at least 65% dissolution, at least 70% dissolution, at least 75% dissolution, at least 80% dissolution, or at least 85% dissolution after incubation in an aqueous acidic solution for at least 45 minutes, at least 40 minutes, at least 35 minutes, at least 30 minutes, at least 25 minutes, at least 20 minutes, or at least 15 minutes.

In some embodiments, the pharmaceutical composition exhibits at least 75% dissolution after 45 minutes in an aqueous solution having a pH from about 1 to 5.5. In some embodiments, the pharmaceutical composition exhibits at least 75% dissolution after 30 minutes in an aqueous solution having a pH from about 1 to 5.5. In some embodiments, the aqueous solution is at a temperature of about 37° C.

In some embodiments, the pharmaceutical composition exhibits at least 75% dissolution after 45 minutes in an aqueous solution having a pH from about 1 to 5. In some embodiments, the pharmaceutical composition exhibits at least 75% dissolution after 30 minutes in an aqueous solution having a pH from about 1 to 5. In some embodiments, the pharmaceutical composition exhibits at least 75% dissolution after 15 minutes in an aqueous solution having a pH from about 1 to 5. In some embodiments, the aqueous solution is at a temperature of about 37° C.

In some embodiments, the pharmaceutical composition exhibits at least 75% dissolution after 45 minutes in an aqueous solution having a pH from about 1 to 4.5. In some embodiments, the pharmaceutical composition exhibits at least 75% dissolution after 30 minutes in an aqueous solution having a pH from about 1 to 4.5. In some embodiments, the pharmaceutical composition exhibits at least 75% dissolution after 15 minutes in an aqueous solution having a pH from about 1 to 4.5. In some embodiments, the pharmaceutical composition exhibits at least 85% dissolution after 15 minutes in an aqueous solution having a pH from about 1 to 4.5. In some embodiments, the aqueous solution is at a temperature of about 37° C.

The dissolution profile of the pharmaceutical composition may be assessed using a United States Pharmacopeia (USP) paddle method. Suitable parameters for the USP paddle method will be readily determined by one skilled in the art. In some embodiments, the dissolution of the pharmaceutical composition is assessed using a USP paddle method at 75 RPM. In some embodiments, the dissolution of the pharmaceutical composition is assessed using a USP paddle method at 75 RPM with a sinker.

In some embodiments, dissolution is assessed using a United States Pharmacopeia (USP) paddle method at 50 RPM to 75 RPM with or without a sinker. In some embodiments, dissolution is assessed using a United States Pharmacopeia (USP) paddle method at 50 RPM with a sinker. In some embodiments, dissolution is assessed using a United States Pharmacopeia (USP) paddle method at 60 RPM with a sinker. In some embodiments, dissolution is assessed using a United States Pharmacopeia (USP) paddle method at 75 RPM with a sinker. In some embodiments, dissolution is assessed using a United States Pharmacopeia (USP) paddle method at 50 RPM without a sinker. In some embodiments, dissolution is assessed using a United States Pharmacopeia (USP) paddle method at 60 RPM without a sinker. In some embodiments, dissolution is assessed using a United States Pharmacopeia (USP) paddle method at 75 RPM without a sinker.

In some embodiments, the pharmaceutical composition is formulated for oral administration (e.g., a tablet or capsule). Accordingly, in some embodiments, the pharmaceutical composition is an oral dosage form. In some embodiments, the pharmaceutical composition is an oral unit dosage form.

In some embodiments, the pharmaceutical composition is formulated as a tablet or a capsule. In some embodiments, the pharmaceutical composition is formulated as a tablet. In some embodiments, the pharmaceutical composition is formulated as an immediate release tablet. In some embodiments, the pharmaceutical composition is formulated as a capsule. In some embodiments, the pharmaceutical composition is formulated as an immediate release capsule.

The pharmaceutical compositions described herein can exhibit enhanced solubility properties. When formulated as an immediate release tablet or an immediate release capsule, the pharmaceutical composition exhibits rapid dissolution for oral delivery in a subject, such as a human. Such dissolution properties may be measured by standard protocols, such as those described by United States Pharmacopeia (USP). The immediate release tablet of the present invention can dissolve by at least 25% in any specified interval, or at least 30, 35, 40, 45, 50, 55, 60, 65, 70, 75, 80, 85, 90, or at least 95% in any specified interval. The specified interval can be measured in minutes or hours. For example, the specified interval can be less than 5 minutes, or less than 6, 7, 8, 9, 10, 11, 12, 13, 14, 15, 16, 17, 18, 19, 20, 25, 30, 35, 40, 45, 50, 55 or less than 60 minutes. The dissolution profile can be determined in an aqueous solution having any suitable pH. For example, the aqueous solution can have a pH of from 1 to 7, or from 1 to 6.5, 1 to 6.0, 1 to 5.5, 1 to 5.0, 1 to 4.5, 1 to 4.0, 1 to 3.5, 1 to 3.0, or a pH from 1 to 2.5. Any combination of dissolution amount, specified interval and pH of the aqueous solution can be useful for determining the dissolution rate of the immediate release tablet of the present invention.

In some embodiments, the pharmaceutical composition comprising Compound I is locally acting in the gastrointestinal tract.

In some embodiments, the pharmaceutical composition is formulated such that Compound I is present in an amount ranging from about 5 mg to about 270 mg. In some embodiments, Compound I is present in an amount of about 5 mg, about 10 mg, about 20 mg, about 40 mg, about 80 mg, about 200 mg, or about 270 mg. In some embodiments, Compound I is present in an amount of about 20 mg, about 80 mg, or about 200 mg. In some embodiments, Compound I is present in an amount of about 20 mg. In some embodiments, Compound I is present in an amount of about 80 mg. In some embodiments, Compound I is present in an amount of about 200 mg. In some embodiments, Compound I is present in an amount of about 270 mg.

In some embodiments, the pharmaceutical composition is formulated such that Compound I is present in an amount of about 20 mg. Accordingly, in some embodiments, the formulation comprises about 20 mg of Compound I; about 41.5 mg microcrystalline cellulose; about 30.5 mg lactose; about 1.0 mg silicon dioxide; about 3.0 mg magnesium stearate; about 4.0 mg L-HPC (e.g., LH-21); and a coating. In some embodiments, the pharmaceutical composition comprises 20 mg of Compound I; 41.5 mg microcrystalline cellulose; 30.5 mg lactose; 1.0 mg hydrophobic colloidal silicon dioxide; 3.0 mg magnesium stearate; 4.0 mg L-HPC LH-21; and a coating. In some embodiments, the formulation comprises about 20 mg of Compound I; about 41.5 mg microcrystalline cellulose; about 30.5 mg lactose monohydrate; about 1.0 mg silicon dioxide; about 3.0 mg magnesium stearate; about 4.0 mg L-HPC (e.g., LH-21); and a coating. In some embodiments, the pharmaceutical composition comprises 20 mg of Compound I; 41.5 mg microcrystalline cellulose; 30.5 mg lactose monohydrate; 1.0 mg hydrophobic colloidal silicon dioxide; 3.0 mg magnesium stearate; 4.0 mg L-HPC LH-21; and a coating. In some embodiments, the pharmaceutical composition is formulated as a 20-mg strength tablet or capsule. In some embodiments, the pharmaceutical composition is formulated as a 20-mg strength tablet.

In some embodiments, the pharmaceutical composition is formulated such that Compound I is present in an amount of about 80 mg. Accordingly, in some embodiments, the formulation comprises about 80 mg of Compound I; about 166 mg microcrystalline cellulose; about 122 mg lactose; about 4.0 mg silicon dioxide; about 12.0 mg magnesium stearate; about 16.0 mg L-HPC LH-21; and a coating. In some embodiments, the pharmaceutical composition comprises 80 mg of Compound I; 166 mg microcrystalline cellulose; 122 mg lactose; 4.0 mg hydrophobic colloidal silicon dioxide; 12.0 mg magnesium stearate; 16.0 mg L-HPC LH-21; and a coating. In some embodiments, the formulation comprises about 80 mg of Compound I; about 166 mg microcrystalline cellulose; about 122 mg lactose monohydrate; about 4.0 mg silicon dioxide; about 12.0 mg magnesium stearate; about 16.0 mg L-HPC LH-21; and a coating. In some embodiments, the pharmaceutical composition comprises 80 mg of Compound I; 166 mg microcrystalline cellulose; 122 mg lactose monohydrate; 4.0 mg hydrophobic colloidal silicon dioxide; 12.0 mg magnesium stearate; 16.0 mg L-HPC LH-21; and a coating. In some embodiments, the pharmaceutical composition is formulated as an 80-mg strength tablet or capsule. In some embodiments, the pharmaceutical composition is formulated as an 80-mg strength tablet.

In some embodiments, the pharmaceutical composition is formulated such that Compound I is present in an amount of about 200 mg. Accordingly, in some embodiments, the formulation comprises about 200 mg of Compound I; about 415 mg microcrystalline cellulose; about 305 mg lactose; about 10 mg silicon dioxide; about 30 mg magnesium stearate; about 40 mg L-HPC LH-21; and a coating. In some embodiments, the pharmaceutical composition comprises 200 mg of Compound I; 415 mg microcrystalline cellulose; 305 mg lactose; 10 mg hydrophobic colloidal silicon dioxide; 30 mg magnesium stearate; 40 mg L-HPC LH-21; and a coating. In some embodiments, the formulation comprises about 200 mg of Compound I; about 415 mg microcrystalline cellulose; about 305 mg lactose monohydrate; about 10 mg silicon dioxide; about 30 mg magnesium stearate; about 40 mg L-HPC LH-21; and a coating. In some embodiments, the pharmaceutical composition comprises 200 mg of Compound I; 415 mg microcrystalline cellulose; 305 mg lactose monohydrate; 10 mg hydrophobic colloidal silicon dioxide; 30 mg magnesium stearate; 40 mg L-HPC LH-21; and a coating. In some embodiments, the pharmaceutical composition is formulated as a 200-mg strength tablet or capsule. In some embodiments, the pharmaceutical composition is formulated as a 200-mg strength tablet.

Methods of Use

Compound I has been shown to be a potent inhibitor of the JAK family of enzymes: JAK1, JAK2, JAK3, and TYK2. Inhibition of the family of JAK enzymes could inhibit signaling of many key pro-inflammatory cytokines. Thus, the pharmaceutical compositions of the disclosure are useful in the treatment of inflammatory diseases (including gastrointestinal inflammatory diseases) such as ulcerative colitis, Crohn's disease, allergic rhinitis, asthma, and chronic obstructive pulmonary disease (COPD).

Compound I has been found to have minimal systemic exposure when administered to the gastrointestinal tract. As described previously in U.S. Pat. No. 9,725,470, the absorption and distribution of Compound I has been extensively profiled in preclinical assays. Compound I tested in cannulated rats showed low absorption into plasma at the portal vein. In addition, Compound I is designed to have its effect at the site of action in the gastrointestinal tract. Compound I exhibited a ratio of exposure in the colon to exposure in plasma in rat greater than about 450. In particular, Compound I has demonstrated significantly higher exposure throughout the gastrointestinal tract than exposure in plasma upon oral dosing in preclinical species. Furthermore, Compound I has been evaluated in healthy human subjects and was found to exhibit high drug concentration in stool samples suggesting significant exposure in the gastrointestinal tract.

Oxazolone-induced colitis is an experimental model that has a histological resemblance to human ulcerative colitis. Compound I demonstrated activity in the oxazolone-induced colitis model in mice. Further, when tested in an immunosuppression model in mice, which probes systemic functional activity, the compound demonstrated minimal effect of immunosuppression at the same dose required to demonstrate efficacy in the oxazolone model. Thus, Compound I demonstrated anti-colitic activity without exhibiting systemic effects in preclinical models.

Compound I, and pharmaceutical compositions comprising Compound I, is useful for a variety of gastrointestinal inflammatory indications that include, but are not limited to, ulcerative colitis (proctosigmoiditis, pancolitis, ulcerative proctitis and left-sided colitis), Crohn's disease, collagenous colitis, lymphocytic colitis, Behcet's disease, celiac disease, checkpoint cancer treatment-induced colitis, (e.g. CTLA-4 inhibitor-induced colitis), ileitis, eosinophilic esophagitis, graft versus host disease-related colitis, and infectious colitis. Ulcerative colitis, Crohn's disease, collagenous colitis, lymphocytic colitis, eosinophilic esophagitis, graft versus host disease-related colitis, infectious colitis, Behcet's disease, celiac disease, checkpoint cancer treatment-induced colitis, and ileitis are characterized by elevation of certain pro-inflammatory cytokine levels. As many pro-inflammatory cytokines signal via JAK activation, the pharmaceutical compositions described herein may be able to alleviate the inflammation and provide symptom relief.

In particular, the pharmaceutical compositions of the disclosure are expected to be useful for the induction and maintenance of remission of ulcerative colitis, and for the treatment of Crohn's disease, CTLA-4 inhibitor-induced colitis, and the gastrointestinal adverse effects in graft versus host disease.

In an aspect, the disclosure provides a method of treating a gastrointestinal inflammatory disease in a mammal (e.g., a human) in need thereof, the method comprising administering to the mammal a therapeutically-effective amount of a pharmaceutical composition of the disclosure.

In some embodiments, the disclosure provides a method of treating inflammatory bowel disease in a mammal, the method comprising administering to the mammal a therapeutically-effective amount of a pharmaceutical composition of the disclosure. In some embodiments, the disclosure provides a method of treating ulcerative colitis in a mammal, the method comprising administering to the mammal a therapeutically-effective amount of a pharmaceutical composition of the disclosure. In some embodiments, the disclosure provides a method of treating Crohn's disease in a mammal, the method comprising administering to the mammal a therapeutically-effective amount of a pharmaceutical composition of the disclosure. In some embodiments, the disclosure provides a method of treating celiac disease in a mammal, the method comprising administering to the mammal a therapeutically-effective amount of a pharmaceutical composition of the disclosure.

In some embodiments, the mammal is a human.

When used to treat a gastrointestinal inflammatory disease, the pharmaceutical compositions disclosed herein will typically be administered orally in a single daily dose or in multiple doses per day, although other forms of administration may be used. Accordingly, in some embodiments, the pharmaceutical composition is administered once daily. In some embodiments, the pharmaceutical composition is administered twice daily. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating ulcerative colitis and other gastrointestinal inflammatory disorders are expected to range from about 1 to about 400 mg/day of Compound I, including from about 5 to about 300 mg/day and from about 20 to about 70 mg per day of active agent for an average 70 kg human. Suitable doses include at least about 0.1 mg/kg, or 0.2, 0.3, 0.4, 0.5, 0.6, 0.7, 0.8, 0.9, 1, 2, 3, 4, 5, 6, 7, 8, 9 or 10 mg/kg. In some embodiments, the subject is administered a pharmaceutical composition comprising Compound I at a dose of at least about 0.1 mg/kg. In some embodiments, the subject is administered a pharmaceutical composition comprising Compound I at a dose of at least about 1 mg/kg. In some embodiments, the subject is administered a pharmaceutical composition comprising Compound I at a dose of about 10 mg/kg. In some embodiments, the subject is administered a pharmaceutical composition comprising Compound I at a dose of from about 0.1 mg/kg to about 10 mg/kg. In some embodiments, the subject is administered a pharmaceutical composition comprising Compound I at a dose of from about 1 mg/kg to about 10 mg/kg. In some embodiments, the subject is administered a pharmaceutical composition comprising Compound I at a dose of from about 0.1 mg/kg to about 1 mg/kg. In some embodiments, the subject is administered a pharmaceutical composition comprising Compound I at a dose of 5 mg, 10 mg, 20 mg, 40 mg, 80 mg, 200 mg, or 270 mg. In some embodiments, the subject is administered a pharmaceutical composition comprising Compound I at a dose of 20 mg, 80 mg, or 200 mg. In some embodiments, the subject is administered a pharmaceutical composition comprising Compound I at a dose of 20 mg. In some embodiments, the subject is administered a pharmaceutical composition comprising Compound I at a dose of 80 mg. In some embodiments, the subject is administered a pharmaceutical composition comprising Compound I at a dose of 200 mg. In some embodiments, the subject is administered a pharmaceutical composition comprising Compound I at a dose of 270 mg.

Combination Therapy

The pharmaceutical compositions disclosed herein may also be used in combination with one or more agents which act by the same mechanism or by different mechanisms to effect treatment of gastrointestinal inflammatory disorders. Useful classes of agents for combination therapy include, but are not limited to, aminosalicylates, steroids, systemic immunosuppressants, anti-TNFα antibodies, anti-VLA-4 antibodies, anti-integrin α4β7 antibodies, anti-bacterial agents, and anti-diarrheal medicines.

In some embodiments, the method further comprises administering one or more additional therapeutic agents. In some embodiments, the one or more additional therapeutic agents are aminosalicylates, steroids, systemic immunosuppressants, anti-TNFα antibodies, anti-VLA-4 antibodies, anti-integrin a4137 antibodies, anti-bacterial agents, or anti-diarrheal medicines.

Aminosalicylates that may be used in combination with the pharmaceutical compositions disclosed herein include, but are not limited to, mesalamine, osalazine and sulfasalazine.

Examples of steroids include, but are not limited to, prednisone, prednisolone, hydrocortisone, budesonide, beclomethasone, and fluticasone. Systemic immunosuppressants useful for treatment of inflammatory disorders include, but are not limited to cyclosporine, azathioprine, methotrexate, 6-mercaptopurine, and tacrolimus.

Further, anti-TNFα antibodies, which include, but are not limited to, infliximab, adalimumab, golimumab, and certolizumab, may be used in combination therapy. Useful compounds acting by other mechanisms include anti-VLA-4 antibodies, such as natalizumab, anti-integrin α4β7 antibodies, such as vedolizumab, anti-bacterial agents, such as rifaximin, and anti-diarrheal medicines, such as loperamide.

In some embodiments, the disclosure provides a therapeutic combination for use in the treatment of gastrointestinal inflammatory disorders, the combination comprising a pharmaceutical composition disclosed herein and one or more other therapeutic agents useful for treating gastrointestinal inflammatory disorders. For example, the disclosure provides a combination comprising a pharmaceutical composition of the disclosure and one or more agents selected from aminosalicylates, steroids, systemic immunosuppressants, anti-TNFα antibodies, anti-VLA-4 antibodies, anti-integrin α4β7 antibodies, anti-bacterial agents, and anti-diarrheal medicines. Secondary agent(s), when included, are present in a therapeutically effective amount, i.e., in any amount that produces a therapeutically beneficial effect when co-administered with a pharmaceutical composition of the present disclosure.

Also provided, therefore, is a pharmaceutical composition of the present disclosure further comprising one or more other therapeutic agents useful for treating gastrointestinal inflammatory disorders.

In some embodiments, the disclosure provides a method of treating gastrointestinal inflammatory disorders, the method comprising administering to the mammal a pharmaceutical composition disclosed herein and one or more other therapeutic agents useful for treating gastrointestinal inflammatory disorders.

When used in combination therapy, the pharmaceutical compositions disclosed herein may further comprise one or more other therapeutic agents (i.e., be formulated in a single pharmaceutical composition). Alternately, the pharmaceutical compositions of the disclosure may be formulated separately from the one or more therapeutic agents, and the separate formulations may be administered simultaneously or at separate times, by the same or by different routes of administration. When administered separately, the formulations are administered sufficiently close in time so as to provide a desired therapeutic effect.

Such formulations can be packaged separately or may be packaged together as a kit. The two or more formulations in the kit may be administered by the same route of administration or by different routes of administration.

Articles of Manufacture and Kits

The pharmaceutical compositions described herein can be prepared, placed in an appropriate container, and labeled for treatment of an indicated condition. Accordingly, there also is contemplated an article of manufacture, such as a container comprising a pharmaceutical composition described herein and a label containing instructions for use of the composition.

In some embodiments, the article of manufacture is a container comprising a pharmaceutical composition described herein. In some embodiments of the articles of manufacture described herein, the pharmaceutical composition is a tablet. In other embodiments of the articles of manufacture described herein, the pharmaceutical composition is an immediate release tablet. In still other embodiments of the articles of manufacture described herein, the pharmaceutical composition is a capsule. In yet other embodiments of the articles of manufacture described herein, the pharmaceutical composition is an immediate release capsule.

Kits are also contemplated. For example, a kit can comprise a pharmaceutical composition of the present disclosure and a package insert containing instructions for use of the composition in treatment of a medical condition. In some embodiments, a kit may comprise multiple pharmaceutical compositions as described herein, each comprising a therapeutically effective amount of Compound I, and instructions for their administration to a human in need thereof.

Methods of Preparation

Particles of crystalline Compound I suitable for the formulations described herein were found to be sticky and difficult to press into tablets. Specifically, amounts of magnesium stearate normally employed in the art provided insufficient glidant properties when coformulated with Compound I. Such formulations resulted in a film of the API forming over the tablet punch after a few tablets had been prepared. Increasing the proportion of magnesium stearate addressed the particular challenges associated with the stickiness of the API; however, this adaption alone caused slower, less uniform dissolution profiles of the resulting tablets. To achieve the rapid, consistent dissolution profiles of the formulations disclosed herein, the manufacturing process was adapted such that particles of the API were first mixed with hydrophobic colloidal silicon dioxide before blending with the remaining excipients. Thus, both the formulation itself and the manufacturing process were optimized to provide the disclosed formulations and dosage forms, which are stable and easy to manufacture on a large scale. In particular, the formulations disclosed herein were found to be suitable for use in continuous manufacturing processes with run times of at least about 2 hours at throughputs of at least about 15 kg/h without any sticking observed in the tablet punch. Accordingly, the disclosure also provides a process for preparing a pharmaceutical composition of the present disclosure.

In some embodiments, the pharmaceutical compositions of the present disclosure are formed by combining the constituent ingredients by known mixing techniques, such as high shear mixing, low shear mixing, and/or blending, such as bin blending, before compressing into tablets and, optionally, coating the tablets.

In some embodiments, the method of preparing a pharmaceutical composition of the disclosure comprises:
(a) combining Compound I and hydrophobic colloidal silicon dioxide together to form a first mixture;
(b) blending microcrystalline cellulose, lactose, and L-HPC together with the first mixture to form a second mixture;
(c) blending magnesium stearate together with the second mixture to form a third mixture; and
(d) compressing the third mixture to form a tablet.

In some embodiments, the method of preparing a pharmaceutical composition of the disclosure comprises:
(a) combining Compound I and hydrophobic colloidal silicon dioxide together to form a first mixture;
(b) blending microcrystalline cellulose, lactose monohydrate, and L-HPC together with the first mixture to form a second mixture;
(c) blending magnesium stearate together with the second mixture to form a third mixture; and
(d) compressing the third mixture to form a tablet.

In some embodiments, Compound I and the hydrophobic colloidal silicon dioxide are blended together via high shear mixing. In some embodiments, Compound I and the hydrophobic colloidal silicon dioxide are blended together via low shear mixing. In some embodiments, the blending is bin blending. In some embodiments, the method further comprises spraying the tablet with a fourth mixture comprising a coating and water.

In some embodiments, the method of preparing a pharmaceutical composition of the disclosure comprises:
(a) combining Compound I and hydrophobic colloidal silicon dioxide together to form a first mixture;
(b) blending microcrystalline cellulose, lactose, and L-HPC together with the first mixture to form a second mixture;
(c) blending magnesium stearate together with the second mixture to form a third mixture;
(d) compressing the third mixture to form a tablet; and
(e) spraying the tablet with a fourth mixture comprising a coating and water.

In some embodiments, the method of preparing a pharmaceutical composition of the disclosure comprises:
(a) combining Compound I and hydrophobic colloidal silicon dioxide together to form a first mixture;
(b) blending microcrystalline cellulose, lactose monohydrate, and L-HPC together with the first mixture to form a second mixture;
(c) blending magnesium stearate together with the second mixture to form a third mixture;
(d) compressing the third mixture to form a tablet; and
(e) spraying the tablet with a fourth mixture comprising a coating and water.

In some embodiments, Compound I and the hydrophobic colloidal silicon dioxide are blended together via high shear mixing. In some embodiments, Compound I and the hydrophobic colloidal silicon dioxide are blended together via low shear mixing. In some embodiments, the blending is bin blending.

In some embodiments, the method of preparing a pharmaceutical composition of the disclosure comprises:
(a) combining Compound I and hydrophobic colloidal silicon dioxide together to form a first mixture;
(b) blending microcrystalline cellulose, lactose, and L-HPC together with the first mixture to form a second mixture; and
(c) blending magnesium stearate together with the second mixture to form a third mixture.

In some embodiments, the method of preparing a pharmaceutical composition of the disclosure comprises:
(a) combining Compound I and hydrophobic colloidal silicon dioxide together to form a first mixture;
(b) blending microcrystalline cellulose, lactose monohydrate, and L-HPC together with the first mixture to form a second mixture; and
(c) blending magnesium stearate together with the second mixture to form a third mixture.

In some embodiments, Compound I and the hydrophobic colloidal silicon dioxide are blended together via high shear mixing. In some embodiments, Compound I and the hydrophobic colloidal silicon dioxide are blended together via low shear mixing. In some embodiments, the blending is bin blending.

EXAMPLES

Abbreviations as used herein have respective meanings as follows:

| | |
|---|---|
| ACN | Acetonitrile |
| API | Active pharmaceutical ingredient |
| aq. | Aqueous |
| CD | Crohn's disease |
| CPV | Crospovidone |
| CCS | Croscarmellose sodium |
| DMF | Dimethylformamide |
| DMSO | Dimethylsulfoxide |
| DSC | Differential scanning calorimetry |
| equiv. or eq. | Equivalents |
| g | Gram |
| h | Hour |
| HPLC | High-pressure liquid chromatography |
| HPC | Hydroxypropyl cellulose |
| Hz | Hertz |
| ifo | In function of |
| kg | Kilogram |
| L | Liter |
| L-HPC | Low-substituted hydroxypropyl cellulose |
| M | Molar |
| MCC | Microcrystalline Cellulose |
| mg | Milligram |
| MGST or MgSt | Magnesium Stearate |
| min | Minute |
| mL | Milliliter |
| mmol | Millimole |
| mol | Mole |
| mo | month |
| mos | months |
| MP | Melting point |
| MS | Mass spectrum |
| NMR | Nuclear Magnetic Resonance |
| RH | Relative humidity |
| RT | Room temperature |
| t-Bu | tert-Butyl |
| TGA | Thermogravimetric analysis |
| vol | Volume |
| wt | Weight |
| XRPD | X-ray powder diffraction |
| μL | Microliter |
| UC | Ulcerative colitis |
| UHPLC | Ultra-high performance liquid chromatography |

Example 1: Preparation and Characterization of Crystalline Compound I

Representative Synthesis of Crystalline Compound I (Form I)

Processes for preparing crystalline Compound I (Form I) are disclosed in U.S. Provisional Patent Application No. 63/089,919, the contents of which are incorporated herein by reference in their entirety.

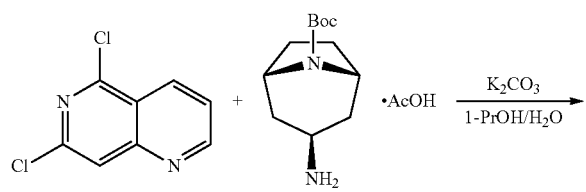

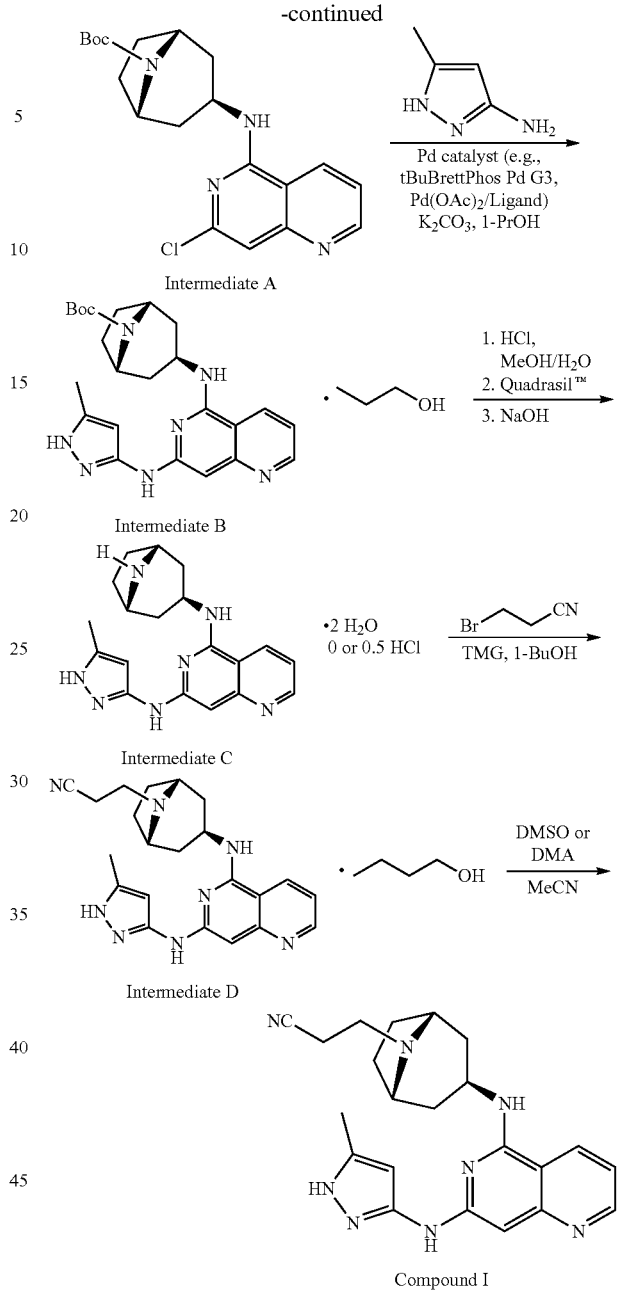

A flask was charged with 5,7-dichloro-1,6-naphthyridine (50.0 g, 251.2 mmol, 1.00 eq), tert-butyl (1R,3s,5S)-3-amino-8-azabicyclo[3.2.1]octane-8-carboxylate·acetic acid (1:1) (79.1 g, 276.3 mmol, 1.10 eq) and K$_2$CO$_3$ (52.1 g, 376.81 mmol, 1.50 eq) followed by the addition of water (250 g) and 1-propanol (80 g). The reaction mixture was heated to 80° C. and stirred for 24 hours at this temperature, then cooled to 20° C. The product was filtered off, washed with a 1:2 mixture of 1-propanol and water and dried at 50° C. under vacuum to yield 91.8 g (236 mmol) of Intermediate A as a light yellow-brown solid in 94% yield. Purity (UHPLC): 99.9%. MS: 389 [M+H]$^+$. Melting point: 226° C.

A flask was charged with Intermediate A (40.0 g, 102.85 mmol, 1.00 eq), 5-methyl-1H-pyrazol-3-amine (11.0 g, 113.14 mmol, 1.10 eq), potassium carbonate (17.1 g, 123.4 mmol, 1.20 eq), and 1-propanol (433 g). Afterward, a solution of [(2-Di-tert-butylphosphino-3,6-dimethoxy-2,4', 6'-triisopropyl-1,1'-biphenyl)-2-(2-amino-1,1'-biphenyl)] palladium (II) methanesulfonate (tBuBrettPhos Pd G3; 0.44 g, 0.5143 mmol, 0.005 eq) in 1-propanol (48 g) was added, and the reaction mixture was heated to 90° C. and stirred for 2 hours at this temperature. The reaction mixture was cooled to 20° C. and stirred for 1 hour at this temperature. Afterward, water (300 g) was added and the reaction mixture was stirred for 2 hours. The product was filtered off and washed first with a 1:1 mixture of 1-propanol and water, and then with water. The wet cake was dried at 50° C. under vacuum to yield 46.35 g of Intermediate B as a yellow, light brown solid in 88% yield. Purity (UHPLC): 99.8%. MS: 450 [M+H]$^+$ (free base). Melting point: 257° C.

A flask was charged with Intermediate B (55.5 g, 108.91 mmol, 1.00 eq), water (134 g) and 1-propanol (11133 g). Afterwards, hydrochloric acid 37% (43.5 g, 436 mmol, 4.0 eq) was added dropwise within 15 min. The resulting reaction mixture was stirred for 15 min at 20° C., heated to 55° C., and then stirred for 3 hours at this temperature. Water (250 g) was added, the reaction temperature was adjusted to 45° C., and the palladium scavenger QuadraSil™ (2.5 g) was added. The mixture was stirred for 1 hour at 45° C. and then cooled to 20° C. Afterward, the palladium scavenger was filtered off and washed with water (25 g). The resulting solution was heated to 45° C., and NaOH 50% (26.1 g, 327 mmol, 3 eq) was added until pH 7-8 was reached. The reaction mixture became turbid. After stirring at 45° C. for 1 hour, NaOH 50% (8.71 g, 109 mmol, 1 eq) was added over 2 hours until pH 12-13 (this pH range affords the dihydrate product—NaOH can, instead, be added until pH 8-10 is reached in order to afford the dihydrate/0.5 hydrochlorate product). The suspension was stirred at 45° C. for 1 hour, then cooled to 20° C. and stirred for 1-2 hours at this temperature. The product was filtered off and the wet cake was washed with a 1:3 mixture of 1-propanol and water and then with water. The product was dried at 50° C. under vacuum to yield 38.28 g of Intermediate C as a yellow orange solid in 91% yield. Purity (UHPLC): 99.9%. MS: 350 [M+H]+ (free base). Melting point: 281° C.

To a reaction flask 1-butanol (51.6 g), Intermediate C (7.02 g, 18.21 mmol, 1.00 eq), and 1,1,3,3-tetramethylguanidine (3.15 g, 27.07 mmol, 1.52 eq) were added. Afterward, 3-bromopropionitrile (3.24 g, 23.94 mmol, 1.32 eq) was dosed within 3 hours while the reaction temperature was kept below 30° C. Traces of 3-bromopropionitrile were rinsed with 1-butanol (5.72 g). The resulting suspension was stirred for 18 hours at 25° C. Then, the reaction mixture was seeded with Intermediate D (0.180 g) and stirred for 1 hour at 25° C. Afterward, water (14.0 g) was added within 30 minutes and the suspension was stirred 18-24 hours. The product was filtered off and the resulting wet cake was washed with a 6:1 mixture of 1-butanol and water and then with water. The wet cake was dried at 50° C. under vacuum to yield 8.79 g of compound Intermediate D as a yellow-orange powder in 99% yield. Purity (UHPLC): 99.8%. MS: 403 [M+H]$^+$ (free base). Melting point: 246° C.

Recrystallization Method 1: In a flask Intermediate D (280.6 g) and dimethyl sulfoxide (1253.8 g) were added, and the mixture was heated to 60° C. for 25 min. The mixture was cooled to 40° C. and acetonitrile (284 mL) was added within minimal 1 hour. The solution was seeded with crystalline Compound I (1.18 g; 0.5%-mol micronized seed crystals) and then stirred for at least 12 hours. Afterward, acetonitrile (2400 mL) was added within 12 hours and the suspension was stirred for an additional 6 hours, cooled to 10° C. within 5 hours, and kept at this temperature for at least 4 hours. The product was filtered off, and the wet cake was washed with acetone (3×880 mL). The wet cake was dried at 45° C. under vacuum to yield 211 g of yellow powder in 89.1% yield. Purity (UHPLC): 99.9%. MS: 403 [M+H]$^+$. Melting point: 249° C. $^1$H NMR (600 MHz, DMSO-d6) δ ppm 1.65-1.75 (m, 2H) 1.75-1.78 (m, 2H) 1.79-1.86 (m, 2H) 1.88-1.97 (m, 2H) 2.21 (s, 3H) 2.63 (s, 4H) 4.54 (br d, J=5.09 Hz, 1H) 6.19 (br s, 1H) 6.65 (br s, 1H) 6.95 (br dd, J=7.72, 3.91 Hz, 1H) 7.13 (br d, J=4.00 Hz, 1H) 8.40 (br d, J=8.17 Hz, 1H) 8.57 (br d, J=3.45 Hz, 1H) 8.73 (br s, 1H) 11.73 (s, 1H).

Recrystallization Method 2: Alternately, in a flask, Intermediate D and dimethyl acetamide (40.14 g) was added, and the mixture was heated to 60° C. for 30. The mixture was cooled to 50° C. and acetonitrile (10.8 mL) was added within minimal 30 min. The solution was seeded with crystalline Compound I (0.010 g; 0.5%-mol micronized seed crystals) and then stirred for at least 12 hours. Afterwards acetonitrile was added in three portions (18.0 mL, 22.0 mL and 49.2 mL) with a duration of 2 h each and an intermediate pause of 1 hour between each dosing step. Afterward, the suspension was stirred for an additional 6 hours, cooled to 5° C. within 8 hours and kept at this temperature for at least 4 hours. The product was filtered off, and the wet cake was washed with acetone (3×30 mL). The wet cake was dried at 45° C. under vacuum to yield 5.35 g of yellow powder in 92% yield. Purity (UHPLC): 99.9%. The MS, melting point and $^1$HNMR align with the data reported immediately above for Compound I.

Characterization of Crystalline Compound I

Figure 2:
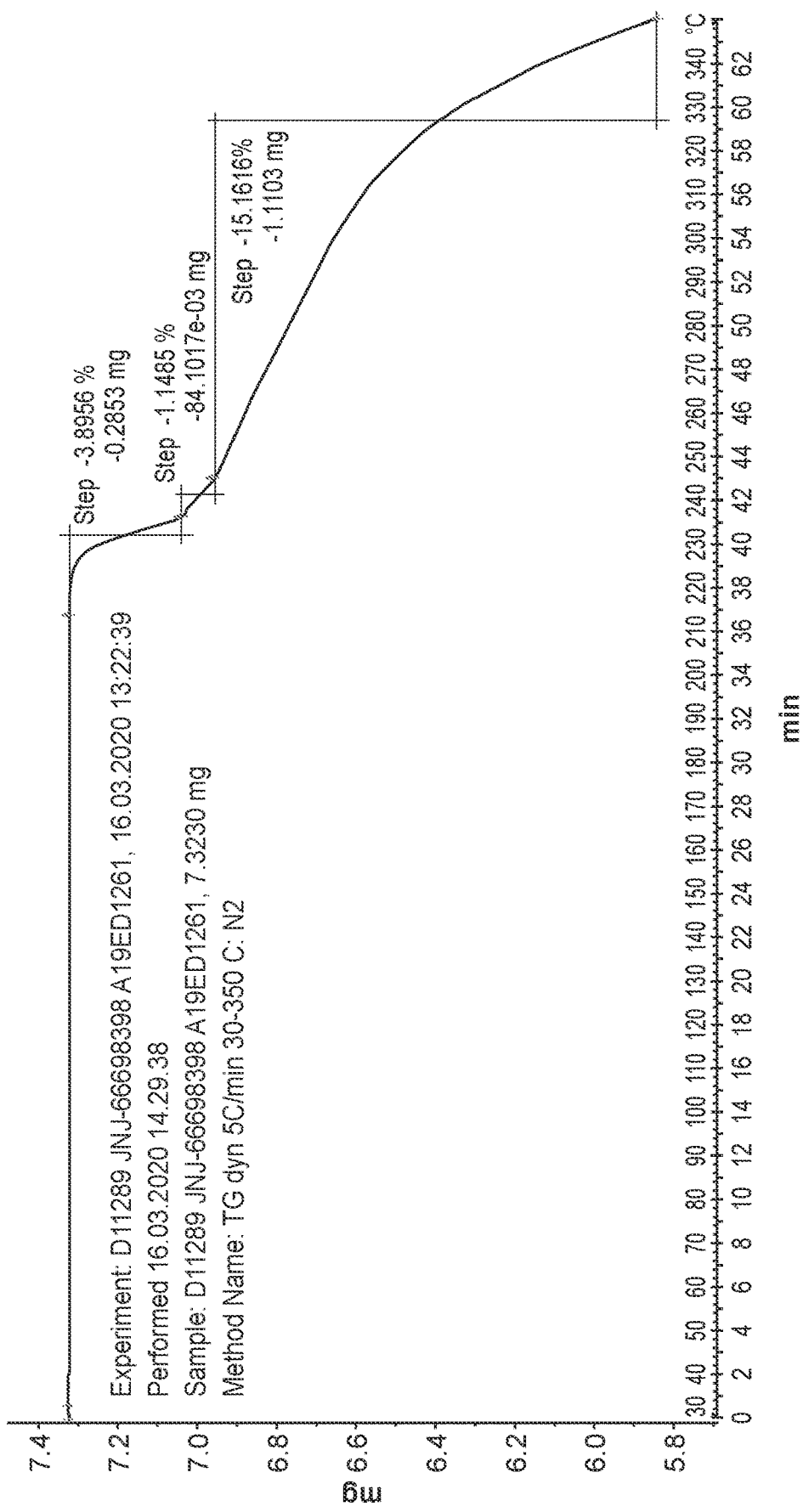
FIG. 2 is a TGA thermogram of Compound I.
Figure 3:
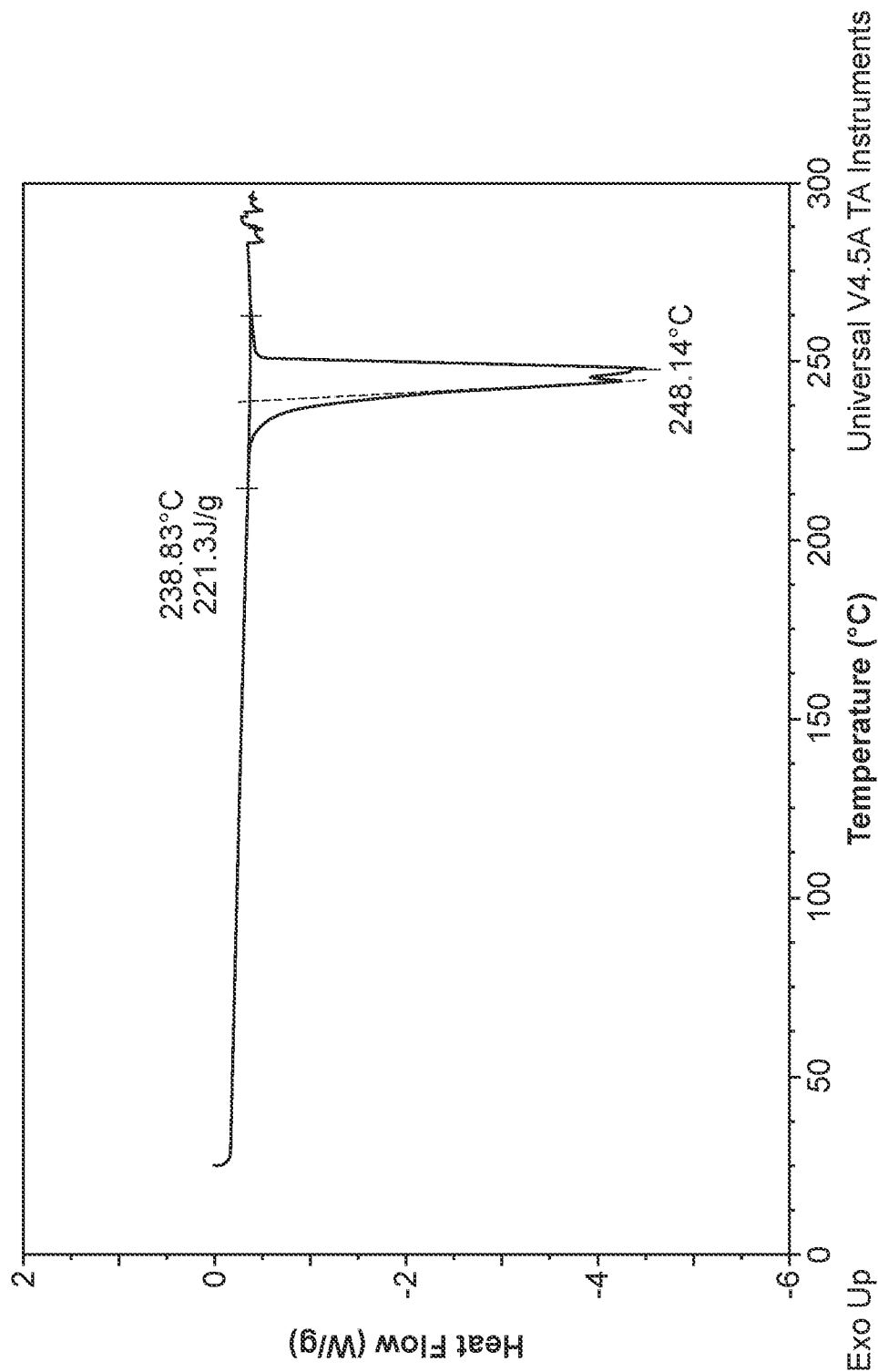
FIG. 3 is an DSC thermogram of Compound. I.

Crystalline Compound I obtained via recrystallization from dimethylsulfoxide and acetonitrile was characterized by an XRPD pattern as shown in FIG. 1. The crystalline compound was further characterized by a thermal gravimetric analysis thermogram as depicted in FIG. 2. The crystalline compound was still further characterized by a differential scanning calorimetry thermogram as depicted in FIG. 3.

Figure 5:
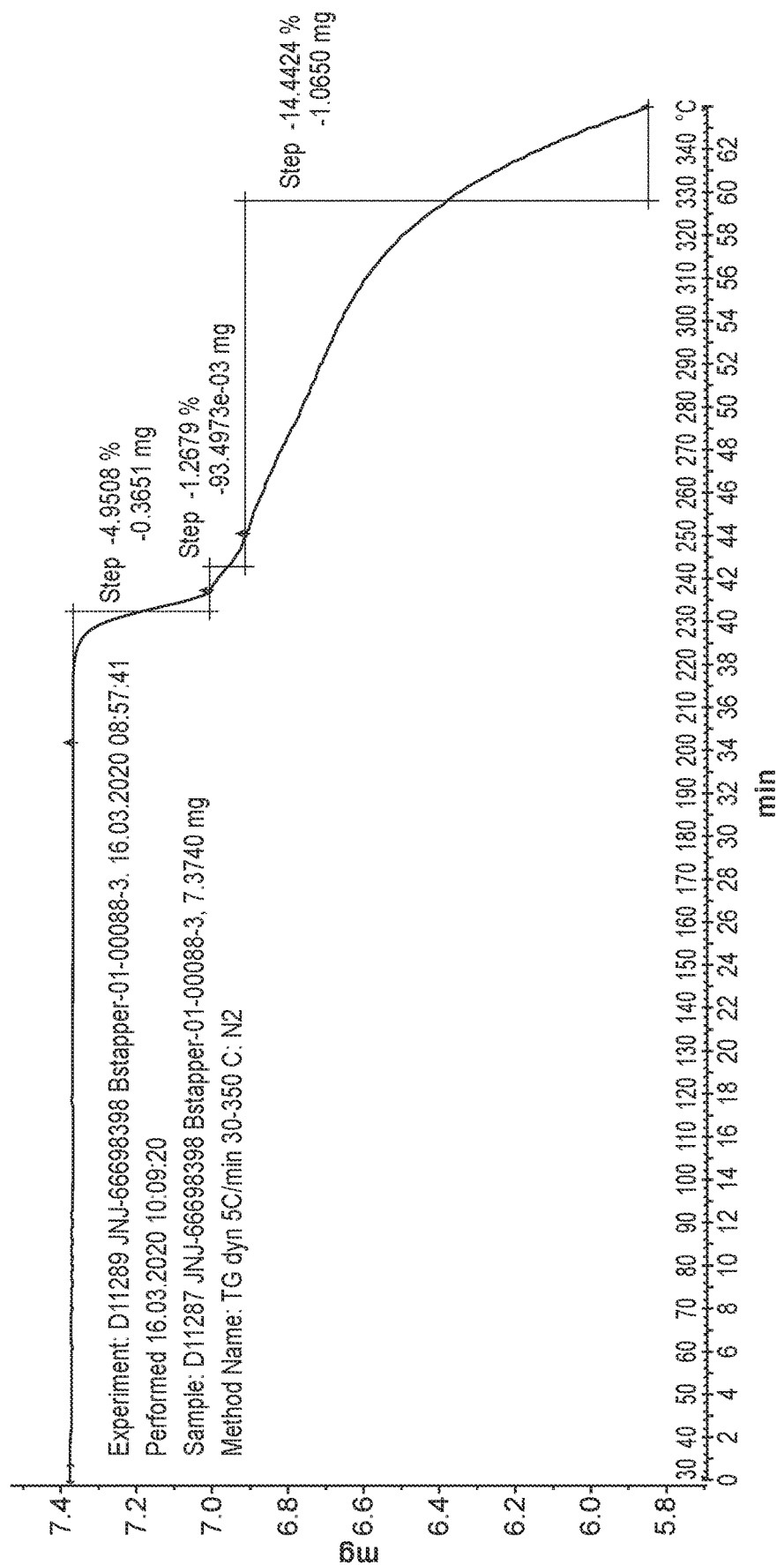
FIG. 5 is a TGA thermogram of Compound I.
Figure 6:
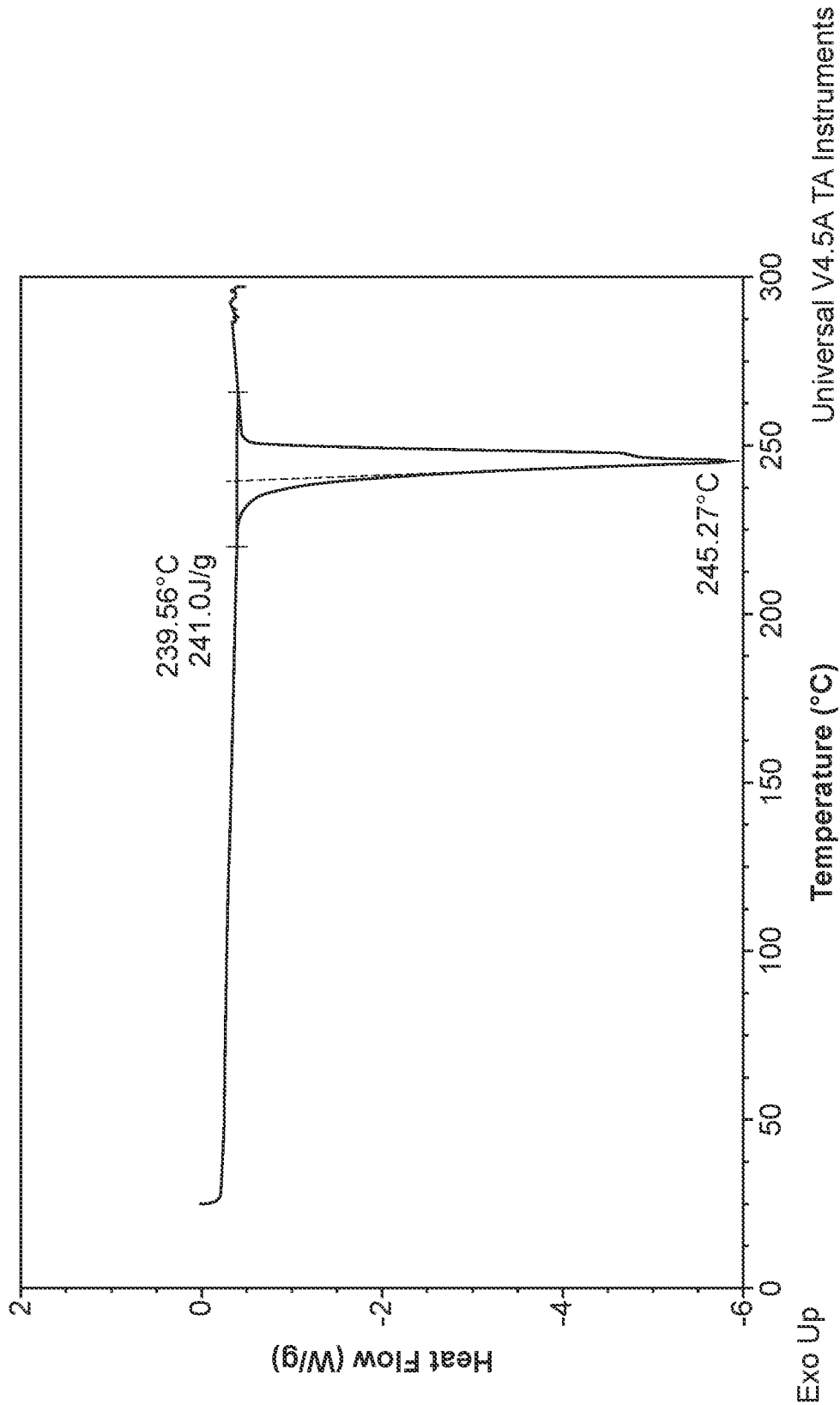
FIG. 6 is an DSC thermogram of Compound. I.

Crystalline Compound I obtained via recrystallization from dimethylacetamide and acetonitrile was characterized by an XRPD pattern as shown in FIG. 4. The crystalline compound was further characterized by a thermal gravimetric analysis thermogram as depicted in FIG. 5. The crystalline compound was still further characterized by a differential scanning calorimetry thermogram as depicted in FIG. 6.

X-Ray Powder Diffraction (XRPD):

The X-ray powder diffraction (XRPD) patterns were obtained with a PANalytical X'PertPRO MPD diffractometer using Cu-Kα radiation (λ=1.54051 Å) with output voltage of 45 kV and current of 40 mA. The instrument was equipped with a Cu LFF X-ray tube and operated in Bragg-Brentano geometry with incident, divergence, and scattering slits set to maximize the intensity at the sample. For measurement, a small amount of powder (approx. 20 mg) was spread on a zero-background sample holder to form a smooth surface and subjected to X-ray exposure. The samples were scanned in continuous mode from 3° to 50° in 2θ with a step size of 0.02° and a scan speed of 30 seconds per step (spinner resolution time 1 sec). The data acquisition was controlled by PANalytical Data Collection software (version 4.4a) software and analyzed by PANalytical Data Viewer 1.9a software (version 1.9a). The instrument was calibrated with a silicon powder reference disc, within: ±0.02° two-theta angle.

Thermo-Gravimetric Analysis (TGA):

The TGA data in FIGS. 2 and 5 were collected on a Mettler Toledo TGA/SDTA 851 thermogravimeter. The instrument parameters described in the following table were used:

| Parameter | Value |
| --- | --- |
| Temperature: | 30° C. |
| Scan rate | 5° C./min |
| Final condition | 350° C. |
| Nitrogen flow ($N_2$) | Yes |

Typically, 3 to 14 mg of each sample was loaded onto a pre-tared aluminum sample pan.

The instrument control software was STARe software (V16.10) (Mettler Toledo).

Differential Scanning calorimetry (DSC).

The DSC data were collected on a TA Instruments Q2000 or Discovery 2500 equipped with a RCS90 cooling unit. The instrument is calibrated for heat flow using an indium reference (±2%), and for temperature using adamantane, octadecane, indium and lead references (±0.5° C.). Typically, about 3 mg of the compound is measured in a standard aluminum sample pan and is heated at 10° C./min from 25° C. to 300° C. The following parameters are used:

| Initial temperature | 25° C. |
| --- | --- |
| Heating Rate | 10° C./min |
| Final temperature | 300° C. |
| Nitrogen flow: | 50 ml/min |

Particle size distributions of crystalline Compound I for use in the pharmaceutical compositions of the disclosure were determined via two separate methods: static image analysis (SIA) and dry dispersion laser diffraction (LD). The applied instrument parameters for each method are described in Tables 1 and 2:

TABLE 1

Static Image Analysis Parameters

| Parameter | Value |
| --- | --- |
| Instrument | Malvern Morphologi G3 |
| Dispersion type | dry |
| Dispersion pressure | 1 bar |
| Lens | 5x (6.5-420 μm) |
| Threshold | manual |
| Z-stacking | no |
| Post-filtering | manual |
| Scan area | 40 mm diameter |

TABLE 2

Dry Dispersion Laser Diffraction Parameters

| Parameter | Value |
| --- | --- |
| Instrument | Malvern Morphologi G3 |
| Module | Aero S |
| Dispersion type | dry |
| Dispersion pressure | 1 bar |
| Venturi type | Standard Venturi Disperser |
| Tray | microtray |
| Feed rate | 30% (can be varied ifo flow) |
| Particle type | Fraunhofer |
| Obscuration | 0.2-15% |
| Auto start | yes (no equilibrium time) |
| Enable filter | yes (3 s time out) |
| Analysis | general purpose |
| Sensitivity | enhanced |
| Keep single result mode | no |
| Fine powder mode | no |

Certain batches of fine particles of crystalline Compound I, Form I were obtained using micronized seed crystals prepared according to Preparation 1 (below); the particle size distributions of these batches are provided in entries 1 to 3 of Table 3. Alternatively, performing the recrystallization reaction with fine seeds of crystalline Form I of Compound I (prepared according to Preparation 2 below) will result in coarse particles crystalline Form I of Compound I with a particle size distribution as provided in entry 4 of Table 3.

TABLE 3

Particle Size of Crystalline Compound I

| Entry/Batch | Static Image Analysis (SIA) | | | Laser Diffraction (LD) | | |
| --- | --- | --- | --- | --- | --- | --- |
| | Dv10 (μm) | Dv50 (μm) | Dv90 (μm) | Dv10 (μm) | Dv50 (μm) | Dv90 (μm) |
| 1 (fine particles) | 12 | 20 | 32 | 4 | 13 | 27 |
| 2 (fine particles) | 15 | 26 | 39 | 4 | 15 | 30 |
| 3 (fine particles) | 13 | 23 | 35 | 4 | 14 | 28 |
| 4 (coarse particles) | 85 | 115 | 143 | 19 | 75 | 136 |
| 5 (intermediate particles) | 40 | 64 | 87 | / | / | / |

The observed difference in absolute values between techniques is the result of the intrinsic difference in measurement principle and the selected instrument parameters. SIA analysis was performed with the 5× lens, which resulted in a lower sensitivity toward fine particles. Alternatively, the LD experiments were performed at a moderate dispersion pressure to fully disperse the material, yet fragmentation of particles cannot be excluded.

Preparation 1 (Micronized Seeds): Preparation of Jet Milled (Micronized) Seeds for Synthesis of Fine Particles of Crystalline Form I of Compound I:

Crystalline Form I of Compound I obtained from a recrystallization procedure described above in Example 1 (Recrystallization Method 1 or 2) was processed by a jet mill (Hosokawa 50 AS Spiral jet mill) operating at a milling/venture pressure of 2 bar. The product was either added manually or via a vibratory feeder (Retsch vibratory feeder DR100). Independent of the feeding operation, a fine yellow powder with a particle size (Dv50) of about 4 to 6 micron was obtained. Use of jet milled (micronized) seeds for the recrystallization procedure described in Recrystallization Method 1 or Method 2 produce fine particles of the crystalline Form I of Compound I. In general, the fine particles of crystalline Form I of Compound I have a particle size (Dv50) of about 18 μm to about 28 μm (e.g., about 20 μm to about 26 μm) as determined by static image analysis and/or a particle size (Dv50) of about 11 μm to about 17 μm (e.g., 13 μm to about 15 μm), as determined by dry dispersion laser diffraction.

Preparation 2 (fine seeds): Preparation of fine seeds for synthesis of coarse particles of crystalline Form I of Compound I: Fine seeds of Compound I (crystalline form I) are obtained by performing the recrystallization with micronized seeds of Compound I, described in Example 1. These fine seeds will have a size range as indicated in Table 3 (see entries 1 to 3). Use of fine seeds for the recrystallization procedure described in Recrystallization Method 1 or Method 2 produce coarse particles of the crystalline Form I of Compound I. In general, these coarse particles have a particle size (Dv50) of about 110 μm to about 120 μm (e.g., about 115 μm to about 117 μm), as determined by static image analysis, and/or a particle size (Dv50) of about 70 μm to about 80 μm (e.g., about 72 μm to about 77 μm), as determined by dry dispersion laser diffraction.

Further manipulation of the seed size is possible by changing the crystallization conditions. More specifically, the amount of antisolvent (acetonitrile) at seeding and the seed temperature can impact the final particle size.

Example 2: Formulation of a Pharmaceutical Composition Comprising Compound I Compound I (1600 g) was combined with hydrophobic colloidal silicon dioxide (Aerosil® R 972; 80 g) by high shear mixing for 10 min. Microcrystalline cellulose (3320 g), lactose monohydrate (2440 g), and low-substituted hydroxypropylcellulose (LH-21; 320 g) were added by bin mixing for 15 min. Magnesium stearate (240 g) was then added by bin mixing for 5 min. The resultant mixture was then compressed into tablets. The formed tablets were each sprayed with a suspension of a polyvinyl alcohol-based film coating (e.g., Opadry AMB II (320 g)) in purified water, before bottling with dessicant.

Exemplary embodiments of the formulation of Compound I are shown in Table 4 below.

TABLE 4

Exemplary pharmaceutical compositions comprising Compound I

| Component | Quantity per Unit (mg) | | |
|---|---|---|---|
| | 20 mg | 80 mg | 200 mg |
| Core Tablet | | | |
| Compound 1 | 20.0 | 80.0 | 200.0 |
| Cellulose, microcrystalline (MCC) | 41.5 | 166.0 | 415.0 |
| Lactose monohydrate | 30.5 | 122.0 | 305.0 |

TABLE 4-continued

Exemplary pharmaceutical compositions comprising Compound I

| Component | Quantity per Unit (mg) | | |
|---|---|---|---|
| | 20 mg | 80 mg | 200 mg |
| L-HPC | 4.0 | 16.0 | 40.0 |
| Silicon dioxide, hydrophobic colloidal | 1.0 | 4.0 | 10.0 |
| Magnesium stearate | 3.0 | 12.0 | 30.0 |
| Core Tablet Weight | 100.0 | 400.0 | 1000.0 |
| Film Coat | | | |
| Opadry ® AMB II 88A620004 Yellow | 4.0 | 16.0 | — |
| Opadry ® AMB II 88A170010 Beige | — | — | 40.0 |
| Total Tablet Weight | 104.0 | 416.0 | 1040.0 |

Details of the batch analysis of the 200-mg tablet is shown in Table 4 above are summarized in Table 5 below, which illustrates the UHPLC profile of the tablet as compared to the Compound I starting drug substance.

TABLE 5

Batch analysis of 200-mg tablet

| Test Parameter | Test Results | |
|---|---|---|
| Assay by UHPLC | Compound I | 200-mg Tablet |
| Compound I (%) | 99.3 | 99.6 |
| Impurity 1 - Compound II (%) | 0.05 | 0.05 |
| Impurity 2 - Compound III (%) | — | <0.05* |
| Impurity 3 - unidentified impurity (%) | 0.05 | 0.05 |
| Total degradation products (%) | 0.10 | 0.10 |
| Water content by Karl Fischer (% w/w) | 0.0 | 3.6 |

*<0.05 means less than 0.05% or not detected

Example 3: Additional Pharmaceutical Compositions Comprising Compound I

Additional 20-mg and 80-mg tablet formulations of Compound I were prepared using an alternate coating and are shown in Table 6,

TABLE 6

Exemplary pharmaceutical compositions comprising Compound I

| Component | Quantity per Unit (mg) | |
|---|---|---|
| | 20 mg | 80 mg |
| Core Tablet | | |
| Compound 1 | 20.0 | 80.0 |
| Cellulose, microcrystalline (MCC) | 41.5 | 166.0 |
| Lactose monohydrate | 30.5 | 122.0 |
| L-HPC | 4.0 | 16.0 |
| Silicon dioxide, hydrophobic colloidal | 1.0 | 4.0 |
| Magnesium stearate | 3.0 | 12.0 |
| Core Tablet Weight | 100.0 | 400.0 |
| Film Coat | | |
| Opadry ® AMB II 88A220061 Yellow | 4.0 | 16.0 |
| Total Tablet Weight | 104.0 | 416.0 |

Example 4: Stability Data of a Pharmaceutical Composition Comprising Compound I

Stability data for the 200-mg tablet of Compound I illustrated in Example 2 above is summarized in Tables 7 and 8 below, which illustrate the UHPLC profile of Compound I within the tablet after storage conditions 30° C./75% relative humidity (RH) (Table 7) or 40° C./75% RH (Table 8) in comparison with the initial profile.

TABLE 7

Stability Analysis of 200-mg tablet at 30° C./75% RH

| Test Parameter | Test Results | | | | | | |
|---|---|---|---|---|---|---|---|
| Assay by UHPLC | Initial | 1 mo | 3 mos | 6 mos | 9 mos | 12 mos | 18 mos |
| Impurity 1 - Compound II (%) | 0.05 | 0.05 | 0.06 | 0.06 | 0.07 | 0.07 | 0.08 |
| Impurity 2 - Compound III (%) | <0.05* | <0.05* | <0.05* | <0.05* | <0.05* | <0.05* | <0.05* |
| Impurity 3 - unidentified impurity (%) | 0.05 | 0.05 | 0.05 | 0.05 | 0.05 | 0.05 | 0.05 |
| Impurity 4 - Compound IV (%) | <0.05* | 0.05 | <0.05* | <0.05* | 0.05 | 0.05 | 0.05 |
| Total degradation products (%) | 0.10 | 0.15 | 0.11 | 0.11 | 0.16 | 0.17 | 0.17 |
| Water content by Karl Fischer (% w/w) | 3.6 | 3.4 | 3.5 | 3.3 | 3.3 | 3.5 | 3.6 |

*<0.05 means less than 0.05% or not detected

TABLE 8

Stability Analysis of 200-mg tablet at 40° C./75% RH

| Test Parameter | | Test Results | | |
|---|---|---|---|---|
| Assay by UHPLC | Initial | 1 month | 3 months | 6 months |
| Impurity 1 - Compound II (%) | 0.05 | 0.06 | 0.07 | 0.08 |
| Impurity 2 - Compound III (%) | <0.05* | <0.05* | <0.05* | <0.05* |
| Impurity 3 - unidentified impurity (%) | 0.05 | 0.05 | 0.05 | 0.05 |
| Impurity 4 - Compound IV (%) | <0.05* | 0.05 | <0.05* | 0.05 |
| Total degradation products (%) | 0.10 | 0.16 | 0.12 | 0.18 |
| Water content by Karl Fischer (% w/w) | 3.6 | 3.5 | 3.4 | 3.4 |

*<0.05 means less than 0.05% or not detected

In the stability experiments summarized in Tables 7 and 8, the 200-mg tablet of Compound I illustrated in Example 2 was placed in a high density polyethylene (HDPE) bottle that is induction sealed with 2 grams of silica gel as a desiccant for moisture protection and closed with a child resistant cap and exposed in a stability chamber at 30° C./75% RH (see Table 7) and at 40° C./75% RH (see Table 8). The degradation of the tablet was then measured at time=0, 1, 3, 6, 9, 12, and 18 months (Table 7) or time=0, 1, 3, and 6 months (Table 8). The visual appearance of the sample tablet in Example 2 was also tested by visual observation and no change was observed at either time=0, 1, 3, 6, 9, 12, and 18 months (Table 7) or time=0, 1, 3, and 6 months (see, e.g., Table 8).

The UHPLC conditions for measuring the data in Tables 5, 7, and 8 were as follows:

Mobile Phases:

Mobile phase A: Water/Trifluoroacetic, 99.6/0.4 v/v

Mobile phase B: Acetonitrile/Trifluoroacetic acid, 99.6/0.4 v/v

Operating Parameters:

TABLE 9

Linear Gradient Program

| Time (Minutes) | Mobile Phase A (% vol.) | Mobile Phase B (% vol.) |
|---|---|---|
| 0 | 90 | 10 |
| 23 | 65 | 35 |
| 25 | 0 | 100 |

TABLE 9-continued

Linear Gradient Program

| Time (Minutes) | Mobile Phase A (% vol.) | Mobile Phase B (% vol.) |
|---|---|---|
| 27 | 0 | 100 |
| 28 | 90 | 10 |
| 32 | 90 | 10 |

Column: Acquity UPLC BEH C18, 150 mm length×2.1 mm i.d., 1.7 μm particle size

Flow rate: 0.35 mL/min

Detection: UV

Wavelength: 253 nm

Column Temperature: 40° C.

Auto-Sampler Temperature: 5° C.

Analysis Run Time: 32 minutes

Example 5: Dissolution Data of a Pharmaceutical Composition Comprising Compound I The analytical method used for dissolution testing is summarized in Table 10:

TABLE 10

Dissolution Testing Parameters

| Parameter | Value |
|---|---|
| Apparatus | Paddle (USP type 2, Ph. Eur. JP) |
| Dissolution medium | 0.05M sodium acetate buffer pH 4.5 |
| Medium temperature | 37.0 ± 0.5° C. |
| Medium volume | 900 mL |
| Paddle rotation speed | 75 rpm |
| Sample filter | Syringe filter 0.45 μm pore size, regenerated cellulose membrane |
| Analytical finish | UHPLC with UV detection at 274 nm |

Dissolution testing of the 200-mg tablet of Compound I illustrated in Example 2 above was performed according to the parameters in Table 10. The tablet exhibited 100% dissolution within 45 minutes.

Example 6: Excipient Compatibility Study

The stability of Compound I when co-formulated with various excipients was assessed at 60° C. at 10% and 75% relative humidity (RH). For example, samples of Compound I (Form I) with different excipient powder blend combinations were stored in an open dish in a glass vial without cap and exposed at 60° C. and 10% RH and at 60° C. and 75% RH. Both binary and multi-excipient powder blends are included at ratios typical for use in solid dosage forms. Samples were evaluated after 28 days of storage and the results compared with results of unstressed Compound I (Form I) and Compound I (Form I) that has been stressed under the same conditions in absence of excipients. The final analysis was performed by UHPLC for chemical purity and visual examination (see, e.g., FIGS. 7A-B and Table 11).

Figure 7A:
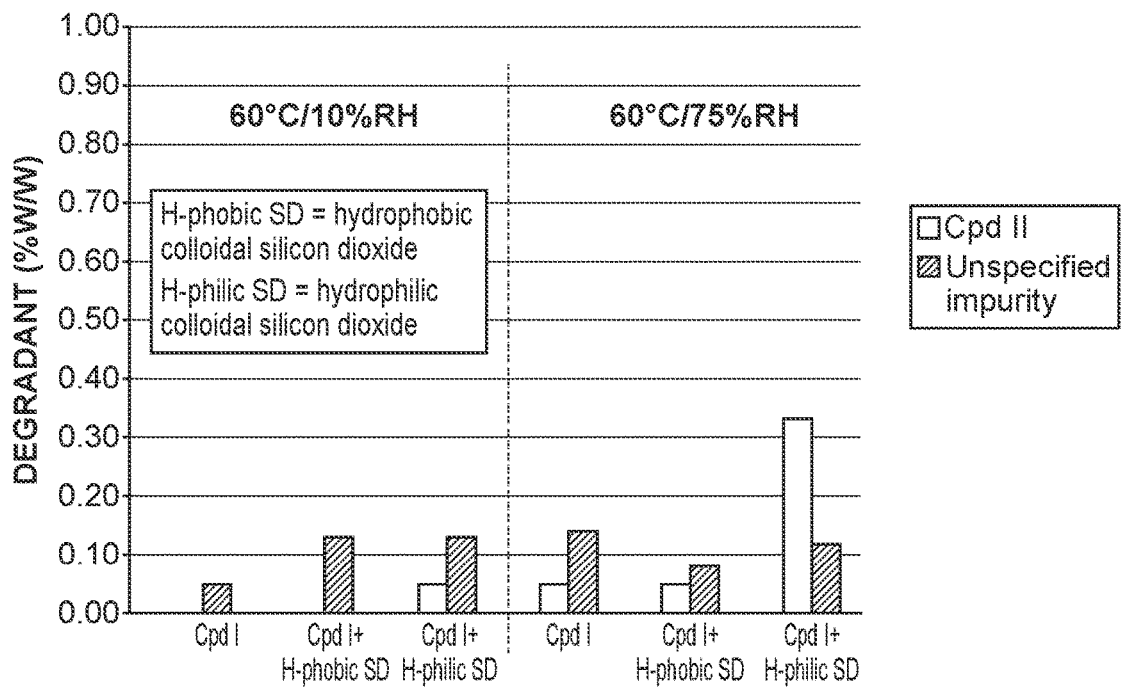
FIG. 7A is a set of bar graphs depicting the formation of degradation products of Compound I when the compound is co-formulated with hydrophobic colloidal silicon dioxide (e.g., Aerosil® R972) or hydrophilic colloidal silicon dioxide (e.g., Aerosil® 200).
Figure 7B:
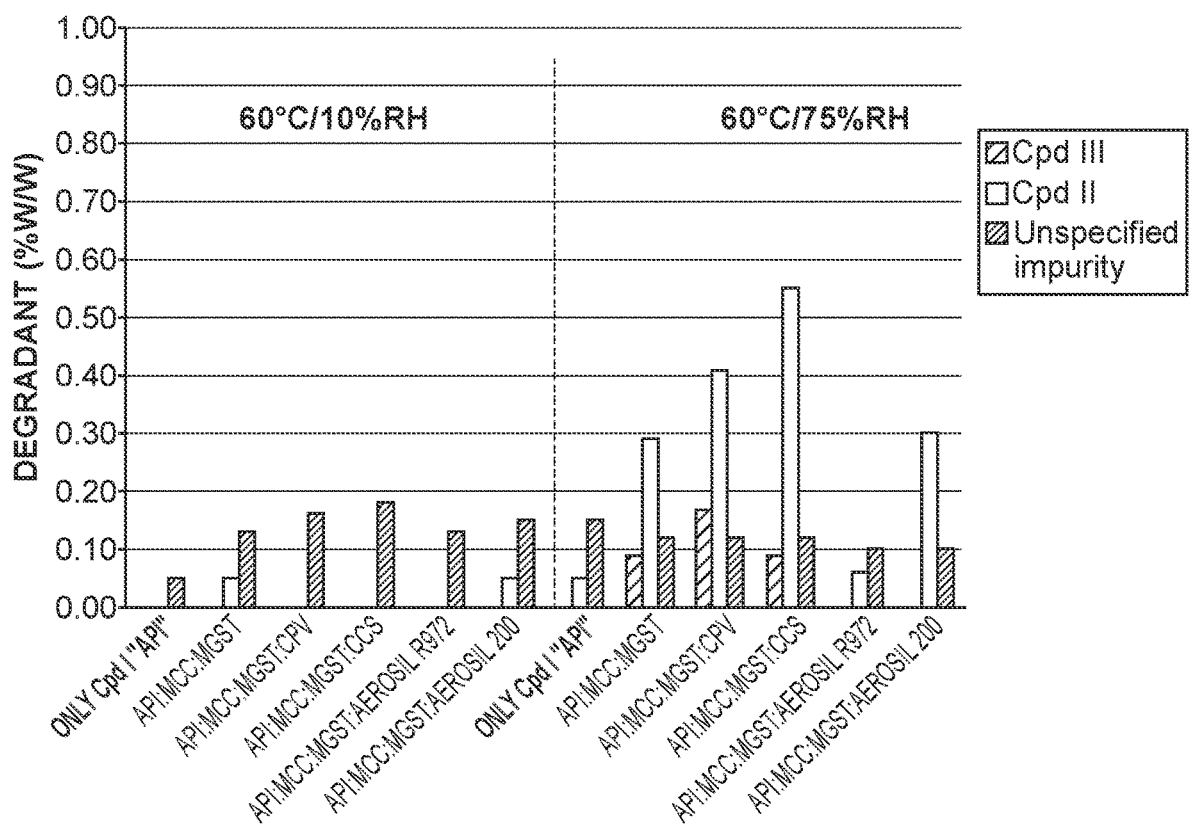
FIG. 7B is a set of bar graphs depicting the formation of degradation products of Compound I when the compound is co-formulated with various combinations of microcrystalline cellulose, magnesium stearate, crospovidone, croscarmellose sodium, hydrophobic colloidal silicon dioxide (e.g., Aerosil® R972), and hydrophilic colloidal silicon dioxide (e.g., Aerosil® 200).

As shown in FIGS. 7A-B, the formation of degradation impurities (e.g., Compound II, Compound III, and/or an unspecified impurity) was determined. For example, FIG. 7A illustrates that the co-formulation of Compound I with hydrophilic colloidal silicon dioxide (Aerosil® 200) resulted in an increased formation of degradation impurities in comparison to the co-formulation of Compound I with hydrophobic colloidal silicon dioxide (Aerosil® R972). Additionally, as shown in FIG. 7B, at 75% RH, co-formulation of Compound I with microcrystalline cellulose (MCC), magnesium stearate (MGST) and one of crospovidone (CPV), croscarmellose sodium (CCS), or hydrophilic colloidal silicon dioxide (Aerosil® 200) resulted in increased formation of degradation impurities. However, co-formulation of Compound I with magnesium stearate, microcrystalline cellulose, and hydrophobic colloidal silicon dioxide (Aerosil® R972) resulted in the formation of minimal impurities. Indeed, the combination of Compound I, magnesium stearate, microcrystalline cellulose, and hydrophobic colloidal silicon dioxide exhibited a degradation profile comparable to that of Compound I alone.

As shown in Table 11, the combination of Compound I with crospovidone (CPV) alone showed comparatively high concentrations of degradation impurity Compound II at 75% RH. The combination of Compound I with croscarmellose sodium (CCS) alone resulted in limited formation of degradation impurity (Compound II) but showed significant discoloration at 75% RH. Finally, the combination of Compound I with L-HPC exhibited a degradation profile comparable to that of Compound I alone and did not show any discoloration (Table 11).

TABLE 11

Effect of stability conditions on the formation of degradation impurity Compound II (% w/w); Absolute differences between Compound I reference versus binary mixtures of Compound I and Disintegrant after 28 days

| Disintegrant | 60%/10% RH | 60%/75% RH | Discoloration |
|---|---|---|---|
| L-HPC | 0 | 0.01 | No |
| CCS | 0 | 0.03 | Yes |
| CPV | 0 | 0.11 | No |

Example 7: Optimization of Lubricant Content and Blending Process

Figure 8:
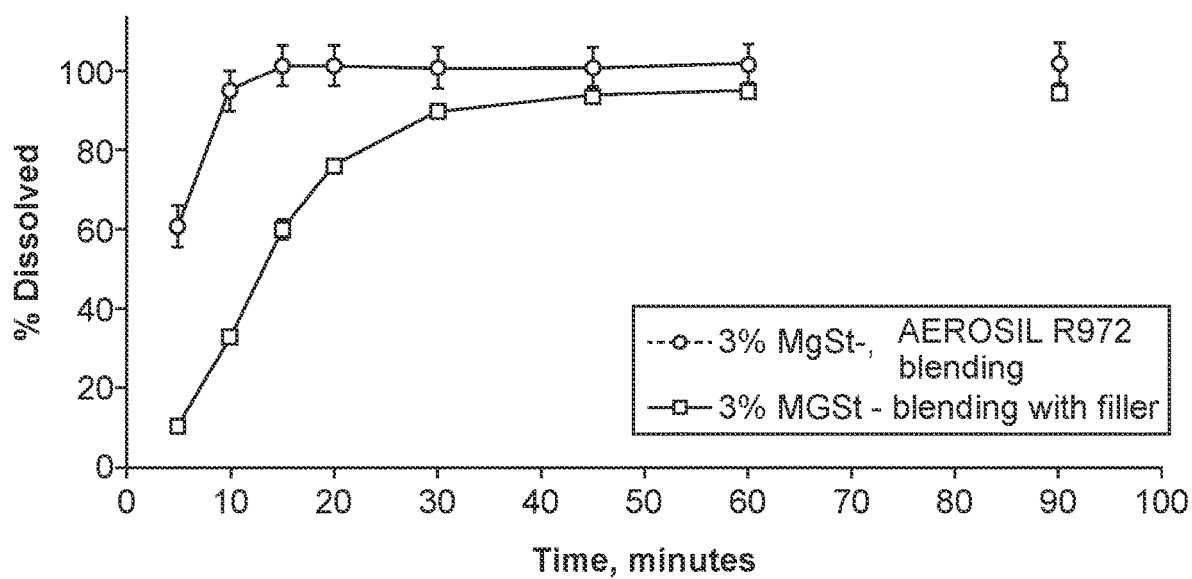
FIG. 8 is a graph depicting the dissolution profile of two 3% magnesium stearate formulations, one in which the particles of Compound I were blended with hydrophobic colloidal silicon dioxide (e.g., Aerosil® R972) before blending with other excipients (circles), and one in which pre-blending with hydrophobic colloidal silicon dioxide did not occur (squares).

During manufacturing of certain tablets comprising 0.5-1% magnesium stearate, film formation on tablet punches was observed. The film formed after compression of a few tablets. After extensive investigation, the problem was resolved by increasing the magnesium stearate content in the composition up to 3%. Although the increase of lubricant concentration resolved the film formation on tablet punches, a reduced dissolution rate of Compound I was observed when blending Compound I particles with a filler (as shown in FIG. 8).

In order to achieve a fast dissolution rate, particles of Compound I were first blended with hydrophobic colloidal silicon dioxide. In doing so, the hydrophobic colloidal silicon dioxide formed a protective layer on the particles of Compound I, thereby reducing layering of magnesium stearate on those particles. The silicon dioxide-coated particles were subsequently blended with the remaining excipients and compressed into tablets.

Figure 9:
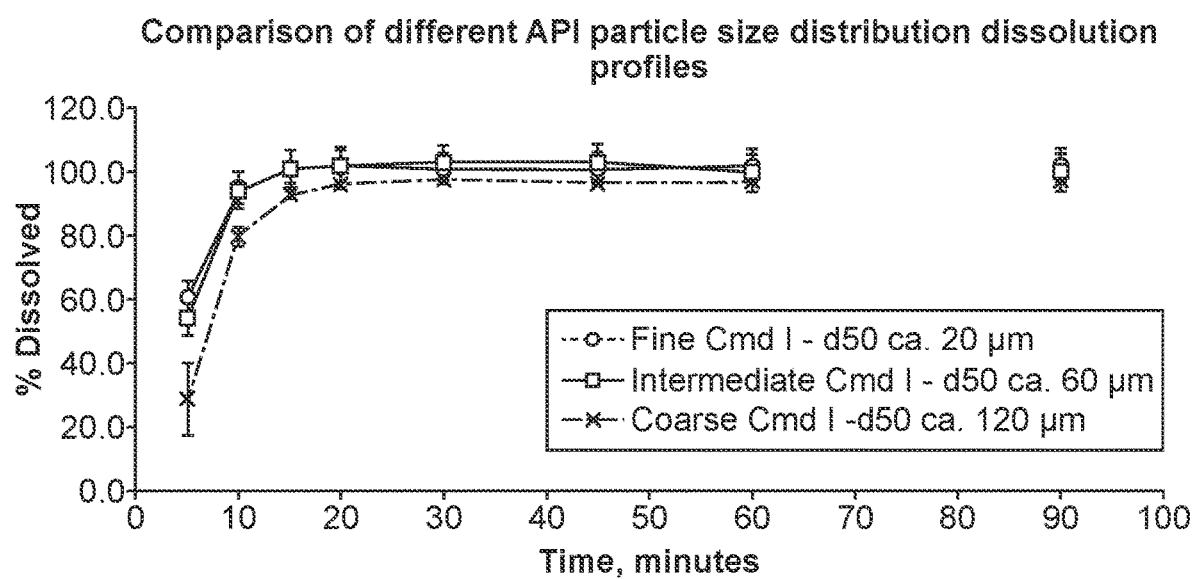
FIG. 9 is a graph depicting the dissolution profiles of three tablets containing 3% magnesium stearate that were prepared by pre-blending varying particle sizes of Compound I (fine particles, circles; intermediate particles, squares; coarse particles, crosses) with hydrophobic colloidal silicon dioxide. The particle size of Compound I was determined by static image analysis.

Using this manufacturing procedure, consistently fast dissolution profiles were obtained for different particle sizes of Compound I without leading to the unwanted film formation on tablet punches. Dissolution profiles of tablets manufactured according to this procedure and containing various particle sizes of Compound I are depicted in FIG. 9. Although tablets made with coarse particles of Compound I (Dv50 of about 110 μm to about 120 μm as determined by static image analysis) exhibited a slight reduction in the dissolution rate as compared to tablets made with finer particles (Dv50 of about 18 μm to about 28 μm as determined by static image analysis) of the API (thereby indicating the upper limit of the particle size), the dissolution performances of all three tablets tested nonetheless qualify as fast dissolving.

Although the pharmaceutical compositions of the disclosure have been described in some detail by way of illustration and example for purposes of clarity of understanding, one of ordinary skill in the art will appreciate that certain changes and modifications may be practiced within the scope of the appended claims. In addition, each reference, including all of the U.S. patents, U.S. patent application publications, U.S. patent applications, foreign patents, foreign patent applications and non-patent publications referred to in this specification are incorporated herein by reference, in their entirety, to the extent not inconsistent with the present description. Where a conflict exists between the instant application and a reference provided herein, the instant application shall dominate.

What is claimed is:

1. A pharmaceutical composition comprising:
Compound I:

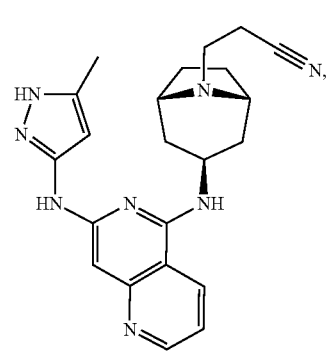 [SMILES: Cc1cc(Nc2cc3ncccc3c(N[C@@H]3C[C@H]4CC[C@@H](C3)N4CCC#N)n2)n[nH]1]

or a pharmaceutically acceptable salt thereof;
microcrystalline cellulose;
lactose;

hydrophobic silicon dioxide;
magnesium stearate;
low-substituted hydroxypropyl cellulose (L-HPC); and
optionally a coating.

2. The pharmaceutical composition of claim 1, comprising
about 10 wt % to about 30 wt % of Compound I, or a pharmaceutically acceptable salt thereof;
about 31.5 wt % to about 51.5 wt % microcrystalline cellulose;
about 20.5 wt % to about 40.5 wt % lactose;
about 0.5 wt % to about 1.5 wt % hydrophobic silicon dioxide;
about 0.5 wt % to about 6.5 wt % magnesium stearate;
about 0.5 wt % to about 7.5 wt % L-HPC; and
optionally a coating.

3. The pharmaceutical composition of claim 1, comprising:
about 20 wt % of Compound I, or a pharmaceutically acceptable salt thereof;
about 41.5 wt % microcrystalline cellulose;
about 30.5 wt % lactose;
about 1.0 wt % hydrophobic silicon dioxide;
about 3.0 wt % magnesium stearate;
about 4.0 wt % L-HPC; and
optionally a coating.

4. The pharmaceutical composition of claim 1, comprising:
20 wt % of Compound I, or a pharmaceutically acceptable salt thereof;
41.5 wt % microcrystalline cellulose;
30.5 wt % lactose;
1.0 wt % hydrophobic silicon dioxide;
3.0 wt % magnesium stearate;
4.0 wt % L-HPC; and
optionally a coating.

5. The pharmaceutical composition of claim 1, wherein Compound I is present in a crystalline form characterized by a XRPD diffractogram having peaks expressed in degrees-2-theta at angles (+0.20) of 7.82, 12.82, 15.76, and 20.51.

6. The pharmaceutical composition of claim 1, wherein Compound I is present in a crystalline form characterized by a XRPD diffractogram having peaks expressed in degrees-2-theta at angles (+0.20) of 7.88, 12.85, 15.80, and 20.41.

7. The pharmaceutical composition of claim 1, wherein the microcrystalline cellulose is partially depolymerized alphacellulose.

8. The pharmaceutical composition of claim 1, wherein the lactose is a spray-dried mixture of crystalline lactose monohydrate and amorphous lactose.

9. The pharmaceutical composition of claim 1, wherein the hydrophobic silicon dioxide is hydrophobic colloidal silicon dioxide.

10. The pharmaceutical composition of claim 9, wherein the hydrophobic colloidal silicon dioxide is fumed silicon dioxide after-treated with dimethyldichlorosilane.

11. The pharmaceutical composition of claim 1, wherein the magnesium stearate has a specific surface area of between 6 and 10 m²/g and a median particle size of between 7 and 11 µm.

12. The pharmaceutical composition of claim 1, wherein the L-HPC has about 10.0% to about 12.9% hydroxypropoxy content and a Dv50 particle size from about 35 µm to about 55 µm.

13. The pharmaceutical composition of claim 1, further comprising a coating.

14. The pharmaceutical composition of claim 13, wherein the coating comprises poly(vinyl alcohol), glycerol monocaprylocaprate type I, titanium dioxide, talc, and sodium lauryl sulfate.

15. The pharmaceutical composition of claim 1, wherein the pharmaceutical composition is substantially free of Compound III, having the following structure:

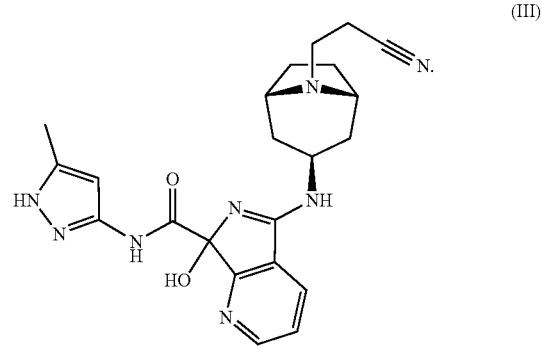 [SMILES: Cc1cc(NC(=O)C2(O)N=C(N[C@@H]3C[C@H]4CC[C@@H](C3)N4CCC#N)c3cccnc32)n[nH]1]

16. The pharmaceutical composition of claim 1, wherein the pharmaceutical composition is substantially free of Compound II, having the following structure:

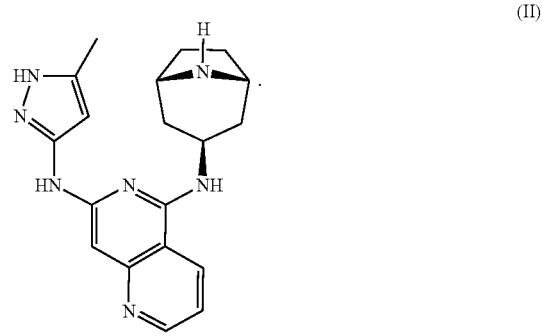 [SMILES: Cc1cc(Nc2cc3ncccc3c(N[C@@H]3C[C@H]4CC[C@@H](C3)N4)n2)n[nH]1]

17. The pharmaceutical composition of claim 1, wherein the pharmaceutical composition is substantially free of Compound IV, having the following structure:

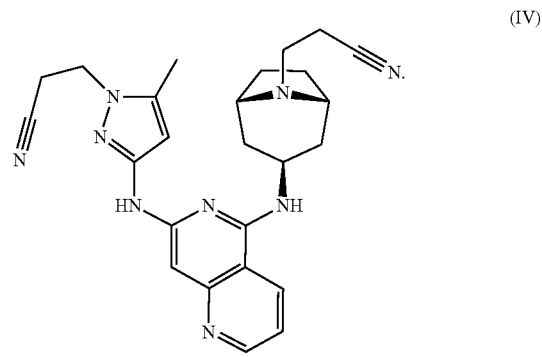 [SMILES: Cc1cc(Nc2cc3ncccc3c(N[C@@H]3C[C@H]4CC[C@@H](C3)N4CCC#N)n2)nn1CCC#N]

18. The pharmaceutical composition of claim 1, wherein the pharmaceutical composition is substantially free of acrylonitrile.

19. The pharmaceutical composition of claim 1, wherein Compound I is present in an amount of about 20 mg.

20. The pharmaceutical composition of claim 1, wherein Compound I is present in an amount of about 80 mg.

21. The pharmaceutical composition of claim 1, wherein Compound I is present in an amount of about 200 mg.

22. The pharmaceutical composition of claim 1, wherein the pharmaceutical composition is a tablet or capsule.

23. A method of treating a gastrointestinal inflammatory disease comprising administering to a mammal in need thereof a therapeutically-effective amount of a pharmaceutical composition of claim 1.

24. A method of preparing the pharmaceutical composition of claim 1 comprising:
- blending Compound I and hydrophobic colloidal silicon dioxide together to form a first mixture;
- blending microcrystalline cellulose, lactose, and L-HPC together with the first mixture to form a second mixture;
- blending magnesium stearate together with the second mixture to form a third mixture;
- compressing the third mixture to form a tablet.

* * * * *